(12) United States Patent
Drmanac et al.

(10) Patent No.: US 7,230,093 B2
(45) Date of Patent: Jun. 12, 2007

(54) METHOD OF SEQUENCING BY HYBRIDIZATION OF OLIGONUCLEOTIDE PROBES

(75) Inventors: Radoje T. Drmanac, Los Altos Hills, CA (US); Radornir Crkvenjakov, Sunnyvale, CA (US)

(73) Assignee: Callida Genomics, Inc., Sunnyvale, CA (US)

( * ) Notice: Subject to any disclaimer, the term of this patent is extended or adjusted under 35 U.S.C. 154(b) by 343 days.

(21) Appl. No.: 10/755,921

(22) Filed: Jan. 12, 2004

(65) Prior Publication Data

US 2004/0235013 A1 Nov. 25, 2004

Related U.S. Application Data

(60) Division of application No. 09/954,426, filed on Sep. 10, 2001, now abandoned, which is a continuation of application No. 09/205,865, filed on Dec. 4, 1998, now Pat. No. 6,316,191, which is a continuation of application No. 08/820,534, filed on Mar. 19, 1997, now abandoned, which is a continuation of application No. 08/460,853, filed on Jun. 5, 1995, now Pat. No. 5,695,940, which is a continuation of application No. 08/203,502, filed on Feb. 28, 1994, now Pat. No. 5,525,464, which is a continuation of application No. 08/048,152, filed on Apr. 15, 1993, now abandoned, which is a continuation of application No. 07/576,550, filed on Aug. 31, 1990, now Pat. No. 5,136,554, which is a continuation of application No. 07/175,088, filed on Mar. 30, 1988, now abandoned.

(30) Foreign Application Priority Data

Apr. 11, 1987 (YU) .................................. P-570/87
Sep. 13, 1987 (YU) ................... 18617/87-P-570/87

(51) Int. Cl.
*C07H 21/04* (2006.01)
(52) U.S. Cl. ......................................... 536/24.3; 435/6
(58) Field of Classification Search .................... None
See application file for complete search history.

(56) References Cited

U.S. PATENT DOCUMENTS 6,018,041 A * 1/2000 Drmanac et al. .......... 536/24.3

OTHER PUBLICATIONS

Asseline et al., "Nucleic acid-binding molecules with high affinity and base sequence specificity: Intercalating agents covalently linked to oligodeoxynucleotides," *Proc. Natl. Acad. Sci. USA* 81:3297-3301 (1984).
Breslauer et al., "Predicting DNA duplex stability from the base sequence," *Proc. Natl. Acad. Sci. USA* 83:3746-3750 (1986).
Craig et al., "Relaxation kinetics of dimmer formation by self complementary oligonucleotides," *J. Mol. Biol.* 62:383-401 (1971).
Estivill and Williamson, "A rapid method to identify cosmids containing rare restriction sites," *Nucl. Acids Res.* 15:1415-1425 (1987).
Ikuta et al., "Dissociation kinetics of 19 base paired oligonucleotide-DNA duplexes containing different single mismatched base pairs," *Nucl. Acids. Res.* 15:79-811 (1987).
Pörschke and Eigen, "Co-operative non-enzymic base recognition," *J. Mol. Biol.* 62:361-381 (1971).
Wallace et al., "Hybridization of synthetic oligodeoxyribonucleotides to $\Phi_x$174 DNA: the effect of single base pair mismatch," *Nucl. Acids Res.* 6:3543-3557 (1979).
Wood et al., "Base composition-independent hybridization in tetramethylammonium chloride: A method for oligonucleotide screening of highly complex gene libraries," *Proc. Natl. Acad. Sci. USA* 82:1585-1588 (1985).

* cited by examiner

*Primary Examiner*—James Ketter
(74) *Attorney, Agent, or Firm*—Marshall, Gerstein & Borun LLP

(57) ABSTRACT

The conditions under which oligonucleotide probes hybridize preferentially with entirely complementary and homologous nucleic acid targets are described. Using these hybridization conditions, overlapping oligonucleotide probes associate with a target nucleic acid. Following washes, positive hybridization signals are used to assemble the sequence of a given nucleic acid fragment. Representative target nucleic acids are applied as dots. Up to to 100,000 probes of the type (A,T,C,G)(A,T,C,G)NB(A,T,C,G) are used to determine sequence information by simultaneous hybridization with nucleic acid molecules bound to a filter. Additional hybridization conditions are provided that allow stringent hybridization of 6–10 nucleotide long oligomers which extends the utility of the invention. A computer process determines the information sequence of the target nucleic acid which can include targets with the complexity of mammalian genomes. Sequence generation can be obtained for a large complex mammalian genome in a single process.

10 Claims, 15 Drawing Sheets

Figure 1A

5'NNNNNNNctggAGTCCCTcggTTGGCTGtagcgAGTCCCTgatTTGGCTGactNNNNNNN3' (SEQ ID NO: 1)

Figure 1B

```
5'NNNNNNNc
   NNNNNNct
    NNNNNNctg
     NNNNNctgg
      NNNNctggA
       NNNctggAG
        NNctggAGT
         NctggAGTC
          ctggAGTCC
           tggAGTCCC
            ggAGTCCCT
             gAGTCCCT
             ─────────
               AGTCCCTc
               AGTCCCTg
```

Figure 1C

```
                        TTGGCTGactNNNNNNN3' (SEQ ID NO: 2)
                 AGTCCCTcggTTGGCTG (SEQ ID NO: 3)
5'NNNNNNNctggAGTCCCT (SEQ ID NO: 4)
                 AGTCCCTgatTTGGCTG (SEQ ID NO: 5)
                       TTGGCTGtagcgAGTCCCT (SEQ ID NO: 6)
```

Figure 1E:

Figure 1D 1)
5'NNNNNNNctggAGTCCCTcggTTGGCTGtagcgAGTCCCTgatTTGGCTGactNNNNNNN3' (SEQ ID NO: 7)
2)
5'NNNNNNNctggAGTCCCTgatTTGGCTGtagcgAGTCCCTcggTTGGCTGactNNNNNNN3' (SEQ ID NO: 8)

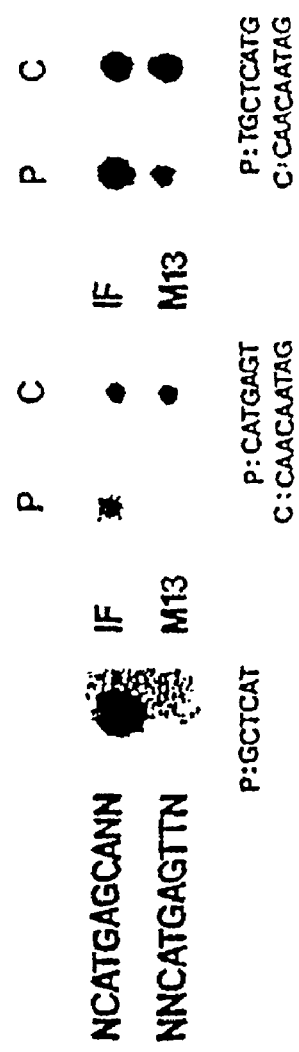
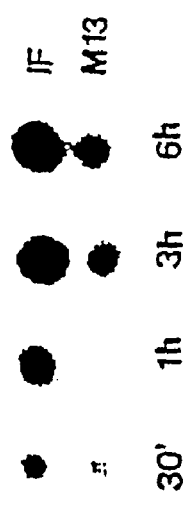
FIG. 4A
FIG. 4B
FIG. 4C

| PROBE | NUMBER OF FULLY MATCHED TARGETS | | NUMBER OF END-BASE MIS-MATCHED TARGETS | | DISCRIMINATION |
|---|---|---|---|---|---|
| | IF | M13 | IF | M13 | |
| CATGAGTT | 1 | – | – | – | 18,3 |
| CCAGTTTT | 1 | – | 3 | 2 | 15,8 |
| ATAGCAAA | 1 | – | 5 | 5 | 1,7 |
| CATGAGT | 1 | – | 2 | 2 | 4,2 |
| GCTCATG | 3 | 1 | 3 | 3 | 2,4 |
| TAGCAAA | 3 | 2 | 18 | 18 | 2,4 |

FIG. 6

FIG. 8 (PART 3)

PART 3 A    IF (+) PROBES

| # | Sequence | Tm | v1 | v2 | | # | Sequence | Tm | v1 | v2 | | # | Sequence | Tm | v1 | v2 | | # | Sequence | Tm | v1 | v2 |
|---|---|---|---|---|---|---|---|---|---|---|---|---|---|---|---|---|---|---|---|---|---|---|
| 1. | GTCTGAAA | 49.5 | 7 | 8 | | 26. | TTCCAGCC | 61.4 | 3 | 5 | | 51. | CAGGAGGT | 55.5 | 7 | 15 | | 76. | GGTTTATC | 55.9 | 5 | 8 |
| 2. | TGTCTGAA | 45.2 | 4 | 8 | | 27. | ATTCCAGC | 59.0 | 7 | 10 | | 52. | CCAGGAGG | 60.0 | 5 | 8 | | 77. | TGGTTTATC | 64.7 | 2 | 3 |
| 3. | TTGTCTGA | 48.2 | 1.5 | 8 | | 28. | CATTCCAG | 53.7 | 3 | 10 | | 53. | GCCAGGAG | 60.1 | 5 | 7 | | 78. | ATGGTTTAT | 64.7 | 5 | 5 |
| 4. | CTTGTCTG | 48.4 | 3 | 15 | | 29. | TCATTCCA | 51.5 | 1 | 3 | | 54. | AGCCAGGA | 60.1 | 8 | 8 | | 79. | GATGGTTT | 55.7 | 7 | 12 |
| 5. | TCTTGTCT | 48.2 | 1 | 3 | | 30. | CTCATTCC | 53.5 | 4 | 8 | | 55. | TAGCCAGG | 60.5 | 6 | 4 | | 80. | AGATGGTT | 54.4 | 5 | 12 |
| 6. | ATCTTGTC | 48.0 | 4 | 15 | | 31. | TCTCATTC | 48.1 | 0.5 | 1.7 | | 56. | TTAGCCAG | 58.6 | 3 | 8 | | 81. | CAGATGGT | 51.1 | 8 | 25 |
| 7. | AATCTTGTC | 58.1 | 10 | 40 | | 32. | GTCTCATT | 49.0 | 5 | 10 | | 57. | ATTAGCCA | 59.4 | 4 | 5 | | 82. | TCAGATGG | 50.2 | 5 | 8 |
| 8. | GAATCTTG | 51.6 | 10 | 40 | | 33. | AGTCTCAT | 47.7 | 1 | 5 | | 58. | CATTAGCC | 59.4 | 2 | 4 | | 83. | TTCAGATG | 48.3 | 8 | 6 |
| 9. | TGAATCTT | 57.4 | 2 | 7 | | 34. | TAGTCTCA | 45.1 | 0.5 | 4 | | 59. | ACATTAGC | 54.9 | 2 | 4 | | 84. | CTTCAGAT | 50.3 | 0.5 | 1.5 |
| 10. | ATGAATCTT | 60.2 | 3.5 | 25 | | 35. | ATAGTCTC | 47.9 | 0.3 | 3 | | 60. | GACATTAG | 49.4 | 5 | 10 | | 85. | TCTTCAGA | 47.3 | 0.5 | 1.3 |
| 11. | GATGAATC | 48.9 | 3 | 25 | | 36. | AATAGTCTC | 57.0 | 7 | 15 | | 61. | AGACATTAG | 57.2 | 10 | 20 | | 86. | GTCTTCAG | 48.2 | 8 | 15 |
| 12. | AGATGAATC | 56.7 | 1.5 | 20 | | 37. | CAATAGTC | 49.1 | 3 | 8 | | 62. | TAGACATTA | 55.4 | 4 | 8 | | 87. | TGTCTTCA | 46.2 | 1 | 3 |
| 13. | TAGATGAAT | 57.1 | 1 | 13 | | 38. | ACAATAGTC | 55.9 | 6 | 15 | | 63. | ATAGACATT | 50.0 | 5 | 8 | | 88. | CTGTCTTC | 48.2 | 1 | 5 |
| 14. | GTAGATGA | 47.2 | 7 | 20 | | 39. | AACAATAGT | 59.1 | 3 | 10 | | 64. | GATAGACA | 45.9 | 10 | 20 | | 89. | ACTGTCTT | 49.1 | 10 | 3 |
| 15. | GCTAGATG | 52.7 | 10 | 20 | | 40. | CAACAATAG | 58.7 | 7 | 20 | | 65. | TGATAGAC | 45.9 | 0.5 | 3 | | 90. | GACTGTCT | 45.6 | 10 | 15 |
| 16. | TGCTAGAT | 52.7 | 0.5 | 3 | | 41. | TCAACAATA | 56.5 | 7 | 15 | | 66. | ATGATAGAC | 54.5 | 10 | 10 | | 91. | GGACTGTC | 48.8 | 10 | 25 |
| 17. | GTGCTAGA | 50.6 | 7 | 30 | | 42. | CTCAACAA | 49.8 | 4 | 12 | | 67. | GATGATAG | 48.0 | 7 | 12 | | 92. | AGGACTGT | 51.0 | 10 | 30 |
| 18. | AGTGCTAG | 52.8 | 5 | 20 | | 43. | TCTCAACA | 46.2 | 2 | 4 | | 68. | TGATGATAG | 53.8 | 5 | 10 | | 93. | CAGGACTG | 50.3 | 10 | 15 |
| 19. | CAGTGCTA | 50.8 | 4 | 8 | | 44. | TTCTCAAC | 49.5 | 0.5 | 9 | | 69. | CTGATGAT | 47.8 | 1 | 4 | | | | | | |
| 20. | CCAGTGCT | 55.8 | 4 | 15 | | 45. | GTTCTCAA | 49.5 | 0.5 | 6 | | 70. | TCTGATGA | 44.8 | 5 | 3 | | | | | | |
| 21. | GCCAGTGC | 59.1 | 10 | 7 | | 46. | GCTTCTCA | 51.4 | 10 | 20 | | 71. | ATCTGATG | 47.8 | 8 | 8 | | | | | | |
| 22. | AGCCAGTG | 55.8 | 5 | 10 | | 47. | AGGTTCTC | 53.4 | 3 | 4 | | 72. | TATCTGATG | 53.8 | 1 | 8 | | | | | | |
| 23. | CAGCCAGT | 55.9 | 5 | 8 | | 48. | GAGGTTCT | 53.4 | 4 | 15 | | 73. | TATCTGAT | 57.6 | 0.5 | 3 | | | | | | |
| 24. | CCAGCCAG | 60.3 | 10 | 15 | | 49. | GGAGGTTC | 56.8 | 8 | 15 | | 74. | TTTATCTGA | 57.6 | 0.5 | 4 | | | | | | |
| 25. | TCCAGCCA | 58.1 | 3 | 5 | | 50. | AGGAGGTT | 53.8 | 7 | 15 | | 75. | GTTTATCTG | 58.5 | 2 | 4 | | | | | | |

| # | Sequence | Tm |
|---|---|---|
| 94. | ATTGTCTG | 49.2 |
| 95. | TAGATGAC | 45.9 |
| 96. | GCCAGCCA | 63.8 |
| 97. | TCCAGCCT | 60.1 |
| 98. | TTCCAGCA | 56.2 |
| 99. | GCATTCCA | 57.0 |
| 100. | TGTCTCAT | 45.7 |
| 101. | TTCTCAAG | 50.8 |
| 102. | GTTCTCAG | 48.2 |
| 103. | TATCTGATT | 57.1 |
| 104. | TTTGTCCT | 58.0 |
| 105. | AGGAGAAA | 56.0 |

FIG. 9

| | | | IF |
| --- | --- | --- | --- |
| Full match | | GACTACTA | ● |
| Control probe | 5' | CTGATGAT 3' | |
| Full match | | GACTACTA | ○ GL |

| | | | IF |
| --- | --- | --- | --- |
| Full match | | CGGTCACG | ● |
| Probe 1 | 5' | GCCAGTGC 3' | |
| End mismatch | | CGGTCACc | ◆ GL |

| | | | IF |
| --- | --- | --- | --- |
| Full match | | CCAAATAG | ● |
| Probe 2 | 5' | GGTTTATC 3' | |
| End mismatch | | gCAAATAG | GL |

| | | | IF |
| --- | --- | --- | --- |
| Full match | | AAGGTCGG | ○ |
| Probe 3 | 5' | TTCCAGCC 3' | |
| End mismatch | | AAGGTCGt | GL |

| | | | IF |
| --- | --- | --- | --- |
| End mismatch | | CAAGAGTt | |
| Probe 4 | 5' | GTTCTCAG 3' | |
| Full match | | CAAGAGTC | ● GL |

# METHOD OF SEQUENCING BY HYBRIDIZATION OF OLIGONUCLEOTIDE PROBES

This application is a divisional application of U.S. application Ser. No. 09/954,426 filed on Sep. 10, 2001 now abandoned, entitled "Methods of Sequencing by Hybridization of Oligonucleotide Probes," which in turn is a continuation application of U.S. application Ser. No. 09/205,865, now U.S. Pat. No. 6,316,191, filed on Dec. 4, 1998, entitled "Computer-aided Analysis System for Sequencing by Hybridization," which in turn is a continuation application of U.S. application Ser. No. 08/820,534 filed Mar. 19, 1997, now abandoned entitled "Methods of Sequencing by Hybridization of Oligonucleotide Probes" which in turn is a continuation application of U.S. application Ser. No. 08/460,853, filed Jun. 5, 1995 now U.S. Pat. No. 5,695,940, entitled "Method of Sequencing by Hybridization of Oligonucleotide Probes," which in turn is a continuation application of U.S. application Ser. No. 08/203,502, filed Feb. 28, 1994 now U.S. Pat. No. 5,525,464, entitled "Method of Sequencing by Hybridization of Oligonucleotide Probes," which in turn is a continuation application of U.S. application Ser. No. 08/048,152 (now abandoned) filed Apr. 15, 1993, entitled "Method of Sequencing by Hybridization of Oligonucleotide Probes," which in turn is a continuation application of U.S. application Ser. No. 07/576,550 (now abandoned) filed Aug. 31, 1990, which in turn is a continuation-in-part application of U.S. application Ser. No. 07/175,088 (now abandoned) filed Mar. 30, 1988, entitled "Method of Sequencing of Genomes by Hybridization of Oligonucleotide Probes,". Priority is claimed to each of the above-identified patent applications, all of which are herein incorporated by reference in their entirety.

1. INTRODUCTION

The present invention belongs to the field of molecular biology. It involves a novel method of sequencing of a target nucleic acid sequence by hybridization of short oligonucleotide probes to a nucleic acid target. The oligonucleotide probes can comprise all known combinations of the four nucleotides of a given length, i.e. oligonucleotides of base composition adenine (A), thymine (T), guanine (G), and cytosine (C) for DNA and A,G,C, and uridine (U) for RNA. Conditions are described which allow hybridization discrimination between oligonucleotides which are as short as six nucleotides long and have a single base end-mismatch with the target sequence.

The invention is demonstrated by way of examples in which sequence information is generated using the method of the invention.

2. BACKGROUND OF THE INVENTION

2.1. Hybridization

Hybridization depends on the pairing of complementary bases in nucleic acids and is a specific tool useful for the general recognition of informational polymers. Diverse research problems using hybridization of synthetic oligonucleotide probes of known sequence include, amongst others, the different techniques of identification of specific clones from cDNA and genomic libraries; detecting single base pair polymorphisms in DNA; generation of mutations by oligonucleotide mutagenesis; and the amplification of nucleic acids in vitro from a single sperm, an extinct organism, or a single virus infecting a single cell.

It is possible to discriminate perfect hybrids from those hybrids containing a single internal mismatch using oligonucleotides 11 to 20 nucleotides in length [Wallace et al., Nucl. Acids Res. 6: 3543 (1979)]. Mismatched hybrids are distinguished an the basis of the difference in the amount of hybrid formed in the hybridization step and/or the amount remaining after the washing steps [Ikuta et al., Nucl. Acids Res. 15: 797 (1987); Thein and Wallace, in Human Genetic Diseases: A Practical Approach, ed. by J. Davies, IRL Press Ltd., oxford, pp. 33–50 (1986)].

The reproducible hybridization of different and diverse short oligonucleotides less than 11 nucleotides long has not been well characterized previously. Detailed hybridization data that allows a constant set of conditions for all predictable oligonucleotides is not available [Besmer et al., J. Mol. Biol. 72: 503 (1972); Smith, in Methods of DNA, and RNA Sequencing, ed. S. Weissman, Praeger Publishers, New York, N.Y., pp. 23–68 (1983); Estivill et al., Nucl. Acids Res. 15: 1415 (1987).

Information is also not available an the effects of a single noncomplementary base pair located at the 5' or 3' end of a hybridizing oligonucleotide that produces a mismatched hybrid when associated with a target nucleic acid. Hybridization conditions that discriminate between (1) a perfectly complementary hybridizing pair of nucleic acid sequences where one partner of the pair is a short oligonucleotide, and (2) a pair wherein a mismatch of one nucleotide occurs on the 5' or 3' end of the oligonucleotide, provide a more stringent environment than is required for internal mismatches because hybrid stability is affected less by a mismatch at the end of a hybridizing pair of complementary nucleic acids than for an internal mismatch.

The length of nucleotides that can distinguish a unique sequence in a nucleic acid of defined size has been predicted [Smith in Methods of DNA and RNA Sequencing, ed. S. Weissman, Praeger Publishers, New York, N.Y., pp. 23–68 (1983)]. Thus random oligonucleotide sequences 16–17 long are expected to occur only once in random DNA of $3 \times 10^9$ bp, the size of the human genome. However, with decreasing probe length, e.g. for oligonucleotides 5 to 10 nucleotides in length, there is an exponential increase in the frequency of occurance within a random DNA of a given size and complexity. Thus, the purposes for which oligonucleotide probes are employed can impact on the length of the oligonucleotides that are used experimentally.

2.2. Conditions for Hybridization Stringency

Wallace et al. [Nucl. Acids Res. 6: 3543 (1979)] describe conditions that differentiate the hybridization of 11 to 17 base long oligonucleotide probes that match perfectly and are completely homologous to the target nucleic acid as compared to similar oligonucleotide probes that contain a single internal base pair mismatch. Wood et al. [Proc. Natl. Acad. Sci. 82: 1585 (19.85)] describe conditions for hybridization of 11 to 20 base long oligonucleotides using 3M tetramethyl ammonium chloride wherein the melting point of the hybrid depends only on the length of the oligonucleotide probe, regardless of its GC content. However, as disclosed in these references eleven mer oligonucleotides are the shortest ones that generally can be hybridized successfully, reliably and reproducibly using known hybridization conditions.

2.3. Sequencing

Nucleic acid sequencing methods, where the position of each base in a nucleic acid molecule in relation to its neighbors is determined to define its primary structure, were developed in the early 1960's for RNA molecules and in the late 1970's for DNA. The two major methods for DNA sequencing, i.e. chemical degradation and dideoxy-chain termination, involve identification and characterization of 1–500 nucleotide long DNA fragments, specific for each one of at least four nucleotide bases, on polyacrylamide gels. The polyacrylamide gels must be able to distinguish single base pair differences in length between fragments. The fragments are generated either by chemical degradation [Maxam-Gilbert, Proc. Natl. Acad. Sci. 74: 560 (1977)] or by dideoxy-chain termination of DNA fragments synthesized by DNA polymerase (Sanger et al., Proc. Natl. Acad. Sci. 74: 5463 (1977)]. A sufficient quantity of isolated fragments is ensured by recombinant DNA technology methods which include cloning, restriction enzyme digestion, gel electrophoresis, and polymerase chain reaction amongst others. These methods allow the identification and amplification of the target DNA to provide material for sequencing.

An intensive amount of manual labor is required in the preparation of appropriate polyacrylamide gels to resolve small differences in fragment size. The speed of sequencing in experienced laboratories throughout the world is approximately 100 bp per person daily. Although the use of electronic robots and computers allows acceleration of the number of base pairs actually determined, preparation of polyacrylamide gels, application of sample, electrophoresis and the subsequent manipulations necessary to obtain high quality autoradiograms that can be read by machines still involve significant intensive, skilled, manual labor for which no substitutes have been found.

2.4. Human Genome Characterization

The genome of higher eucaryotes has up to a million times greater physical complexity than is the complexity of individual genes it encodes, giving it a a corresponding huge informational complexity. From the present knowledge of genome organization and biochemical, biophysical and biological functions, the following approximate scale of the informational complexity for higher eucaryotes can be proposed: 10,000 gene families—100,000 genes—1,000,000 biological functions. The number of basic biochemical functions represented by a single gene family is probably not significantly increased compared to procaryotic and lower eucaryotic genomes.

Recently, there has been a surge of interest in mapping and sequencing the entire human genome [Lewin, Science 232: 1598 (1986); Wada, Nature 325: 771 (1987); Smith and Hood, Bio/Technology 5: 933–939 (1987)]. This stems from the fact that only 1 in about 75 human genes is either cloned or mapped (Human Gene Mapping 9, 1987). Unknown genes will have much to tell us about human biology. In the future, the progress of studies on molecular evolution may depend on the sequencing of genomes of species besides humans.

Because sequence information has already provided accelerated knowledge and potential resolution of diverse biological, medical and therapeutic research problems, it is not surprising that ideas of sequencing the whole human genome were discussed at various scientific meetings during the early and mid-1980's [Research News in Science 232: 1598 (1986)]. Such massive sequencing projects envision the final determination of approximately 3 billion base pairs of information encoded in the DNA of humans and are expected to take at least 10 years at a cost of at least $3 billion dollars using current technology. However, in practice, actual sequencing of at least three times that number of base pairs is required to obtain a reliable sequence for the human genome, thus requiring even more money and time.

Such endeavors present a challenge to the technology of the twentieth century. Further challenges arise if sequencing projects are extended to include the determination of the genomic sequences of characteristic individuals or species of organisms, especially those that have economic, social or medical importance. Such sequencing projects would advance not only our understanding of the evolution of organisms and the evolution of biochemical processes, but would also further the detection, treatment and understanding of disease, and would aid agriculture, the food industry and biotechnology in general. However beneficial the results of such projects would be, their successful completion requires the development of a new, rapid, reproducible and reliable sequencing method such as those described in this invention.

Although the ultimate goal of human genome characterization is the determination of sequence information, progress in characterizing portions of the human genome or the genome of other organisms have been achieved in several areas. A linkage map of the human genome based on cloned DNA probes detecting RFLPs has been obtained [Donis-Keller et al., Cell 51: 319–337 (1987)]. Once mapped, a gene can be approached from a neighboring DNA marker not only by walking [Cross et al., Trends Genet. 2: 174 (1986)] but also by the use of jumping [Collins+Weissman, Proc. Natl'l. Acad. Sci. USA 81: 6812. (1984); Poustka et al., Nature 325: 353 (1987)] and linking [Poustka et al., Trends Genet, 2: 174 (1986)] libraries. The task of going from a marker to a mapped gene is facilitated immensely if an ordered collection of overlapping cosmid or phage clones representing individual chromosomes is available. Attempts to provide a library of overlapping clones using similarities in their patterns of restriction digests have been tried [Coulson et al., Proc. Natl. Acad. Sci. USA 83: 7821 (1986); Olson et al., Proc. Natl. Acad. Sci. USA 83: 7826 (1986); Kohara et al., Cell 50: 495 (1987)]. Alternatively, the hybridization of a collection of 100 specific oligonucleotides to an array of $3–10\times10^6$ cosmid-containing colonies on filters has been proposed. The resulting patterns of hybridization identify specific regions along the genome to which a small collection of cosmids from chromosome libraries can be fitted in the second step [Poustka et al., Cold Spring Harbor Symp. Quant. Biol. 51: 351 (1986); Craig et al., in Human Genetics, Proceedings of the 7th International Congress, Berlin, (1986); Michiels et al., CABIOS 3: 203 (1987)]. Such identification however does not provide desired and useful sequence information of the DNA in a particular identified fragment.

In the area of human genetics, the emphasis is on an individual's DNA and the methods to detect patterns of its variation and inheritance which may influence the determination of a patient's chances for health or disease. The number of genetic regions to be scored in the DNA of an individual requires a large number of polymorphic probes and makes the use of traditional Southern blotting unpractical. However, a method that is capable of amplifying 1000-bp stretches of DNA starting from two flanking oligonucleotide primers and that requires DNA from only 150 cells of an individual has been described recently as well as oligonucleotide probes that can detect mutants in amplified DNA in dot blot hybridization [Saiki et al., Science 239: 487 (1986)]. Both the method of rdering cosmid libraries and the method of amplifying DNA use the work of Wallace for conditions of hybridization that only allowed oligonucleotides of almost perfect homology to their target DNA to hybridize at all [Wallace et al., Nucl. Acids Res.: 3543 (1979)]. In these conditions, almost perfect homology means that the perfect homology has to exist at least in the central part of the hybridizing oligonucleotide/target duplex.

3. SUMMARY OF THE INVENTION

The present invention provides a new method of sequencing that is ideally suited to the sequencing of large complex genomes because it avoids the intensive manual labor involved in resolving gel fragments by size on polyacrylamide gels. The present invention provides methods for sequencing a target nucleic acid by hybridization of overlapping short oligonucleotide probes of known or predicted sequence to the nucleic acid target serially or simultaneously. The oligomer probes of a given size can contain all or most existing combinations of nucleotides for complete sequencing and a part of all possible variants for partial sequencing. Probes can also be composed of oligomers of different sizes as well as comprising all known combinations of nucleotides that are possible for that size oligonucleotide. As the size of the probes that are used decreases, hybridization conditions that are still able to distinguish between mismatched and perfectly matched short oligonucleotides must be used.

In one embodiment of the invention, multiple oligonucleotides that are 11 nucleotides long or longer are hybridized to the target sequence. Hybridization occurs using conditions which are controlled and varied to ensure discrimination between perfectly matched oligonucleotides and oligonucleotides having a one base pair mismatch with the target sequence where the mismatch is located at either one of two ends of the oligonucleotide.

In an theroembodiment of the invention, as an alternative to previous numerous conditions each specific for different sizes and sequences of probes, a single, or few, sets of conditions is invented for all lengths and sequence of probes. These hybridization conditions allow discrimination between perfectly matched and mismatched oligonucleotides that are as short as six nucleotides long. The conditions allow discrimination between a perfectly matching oligonucleotide and one that has a single base mismatch as compared to the target sequence, the mismatch being located at one of the ends of the oligonucleotide.

Following the detection of hybridization of perfectly matched oligonucleotides of known sequence, the sequence of the target nucleic acid is generated by an algorithm using the principle of maximal nonidentical overlap of probe.

In determining sequence by hybridization, oligonucleotides are prepared, target fragments are prepared appropriate for the length of oligonucleotide used for hybridization, and hybridization of the target with all the oligonucleotides occurs under defined conditions that allow discrimination in binding of perfectly matched complementary oligonucleotides and mismatched oligonucleotides. The relationship of probe size and target length is defined and allows complete sequencing of genomes. The novel theoretical basis of the relationship between, oligonucleotide probe size and target length is described infra.

To determine the amount of hybridization data that is needed for sequence determination, the number of target fragments that compose the entire sequence is multiplied by the number of different oligonucleotides required to define the sequence of the target fragment. The shorter the size of the oligonucleotides that are hybridized, the more target fragments that must be analyzed. Similarly, as the oligonucleotide size increases, fewer target fragments must be examined.

Hybridization reactions can be performed in separate reaction vessels or by binding one of the two components (oligomers and DNA fragments) to a solid surface, like nylon filters etc. Since the described method does not require macromolecular separation like gel-based sequencing methods, the surface, bound with either an oligomer or nucleic acid fragment can have microdimensions.

Some of the advantages of the method of the present invention include the following:

(1) rapidity, resulting in time effectiveness; (2) elimination of polyacrylamide gel electrophoresis and the intensive manual labor it requires; (3) reliability of the predicted base within the determined sequence due to the hybridization of multiple oligonucleotides to the same base within a target sequence; (4) the possibility of substantial miniaturization of the process; (5) ease of automation: (6) resulting cost effectiveness.

3.1. Definitions

The following terms and abbreviations will have the meanings indicated:

| | |
|---|---|
| A | adenine |
| bp | base pair |
| C | cytosine |
| G | guanine |
| IF | an H13 clone containing a 921 bp EcoR1-BglII human $\beta_1$ interferon fragment |
| kD | kilo Dalton |
| nG | nanogram |
| nM | nenomolar |
| pmol | pic mole |
| sc | subclone |
| SF | subfragment |
| SOH | short oligonucleotide hybridization |
| T | thymine |
| CCD | Charge Coupled Device |
| DNA | Deoxyribonucleic acid |
| DP | Discrete particle |
| HA | Hybridization area |
| LAR | Ligation-amplification reaction |
| ON | Oligonucleotide |
| ONP | Oligonucleotide probe |
| ONS | Oligonucleotide sequence |
| PCR | Polymerase chain reaction |
| RE | Restriction Enzyme |
| RFLP | Restriction fragment length polymorphism |
| RNA | Ribonucleic acid |
| SBH | Sequencing by hybridization |

4. DESCRIPTION OF THE FIGURES

FIG. 1 shows the generation of subfragments in sequence by, hybridization and their ordering. (A) The sequence of a hypothetical clone. NNNNNNN-ends of vector sequence. AGTCCCT and TTGGCTG are the only oligonucleotides 7 bp or longer repeated within the depicted sequence. (B) Formation of subfragments. Assuming that the content of 8-mers for the depicted sequence is known, these 8-mers are ordered by maximal overlap, in this case 7 bp. Starting from the 5' 8-mer, (NNNNNNNc), ordering is unambiguous up to gAGTCCCT, which on its 3' end contains a repeated 7-mer. The large capitals denote overlapping sequences shared by different oligonucleotides, while the small letters denote unshared bases. Both AGTCCCTc and AGTCCCTg can be overlapped with gAGTCCCT preventing further ordering. Each of the two sequences serves as a starting point for new ordering (not shown). Therefore, each repeated sequence 7 bp or longer represents a branching point. Unambiguous sequences are obtained between two consecutive branching points only. (C) Listing of subfragments formed from 8-mers of depicted sequence. Subfragments are horizontally displaced to indicate overlap; the orientation is 5' to 3' and end subfragments are identifiable. (D) The subfragments cannot be unambiguously ordered into a starting sequence without additional information. Both arrangements shown are possible since subfragments AGTCCCTcggTTGGCTG (SEQ ID NO:3) and AGTCCCTgatTTGGCTG (SEQ ID NO:5) have the same 7-mers at their 5' and 3' ends, respectively. (E) Building the sequence from oligonucleotide blocks. The left box represents all 8-mer oligosequences which occur in 15 base long DNA molecule of unknown sequence (NNN . . . NNN), 8-mers can be ordered by 7 base overlap (right box). Each 7 oligomer extends the sequence of the starting 8-mer ACCGTAAA by one base. Thus, the sequence is generated by uniquely overlapped oligomer blocks.

Figure 2:
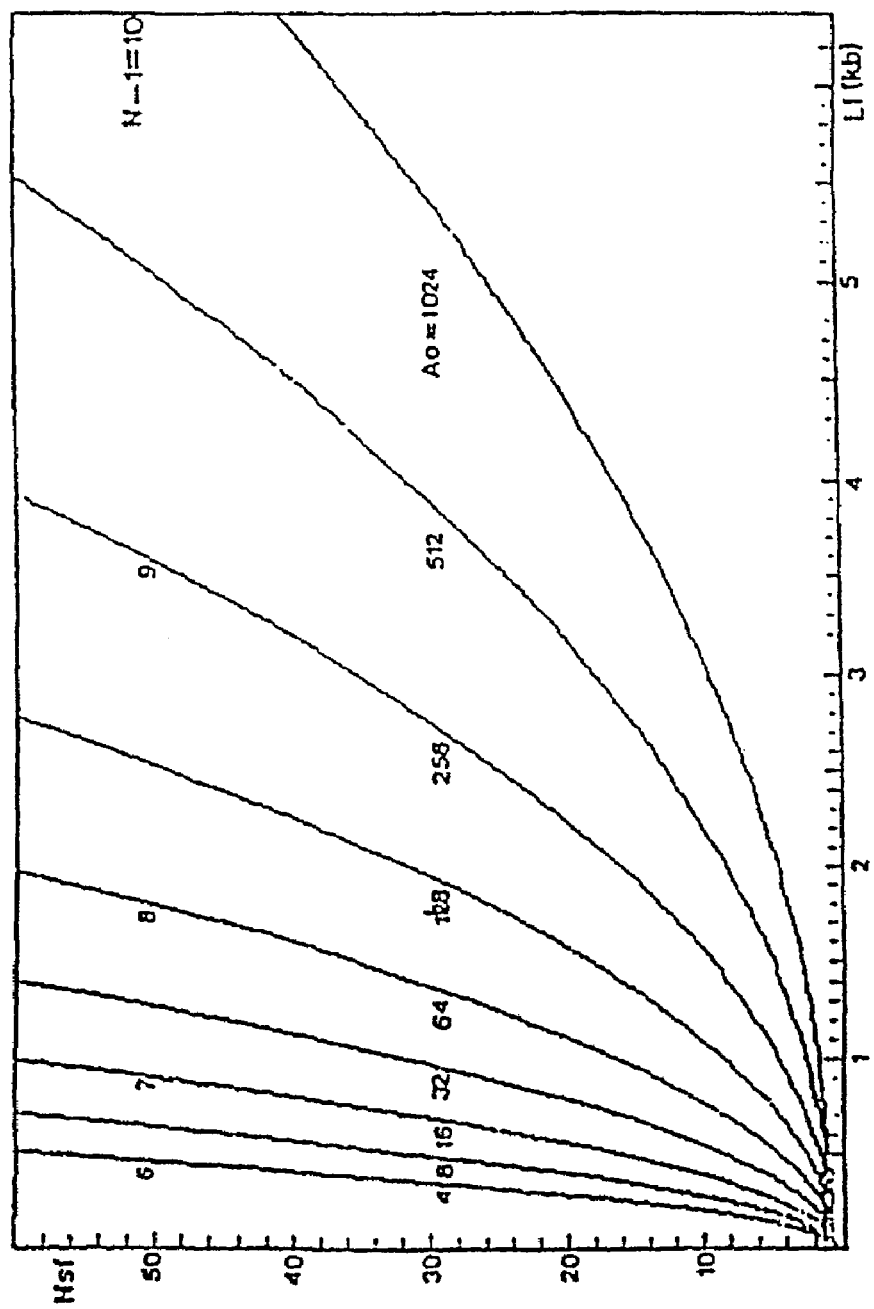

FIG. 2 presents the average number of SFs ($N_{sf}$) as a function of the length of DNA fragment ($L_f$) for various values of the length of the overlapping sequence (N−1, in bp), or average distance of two consecutive identical N−1 sequences in DNA subjected to sequencing by hybridization ($A_o$), in kb. The curves are obtained using equation one as described below in section 5.2.

Figure 3:
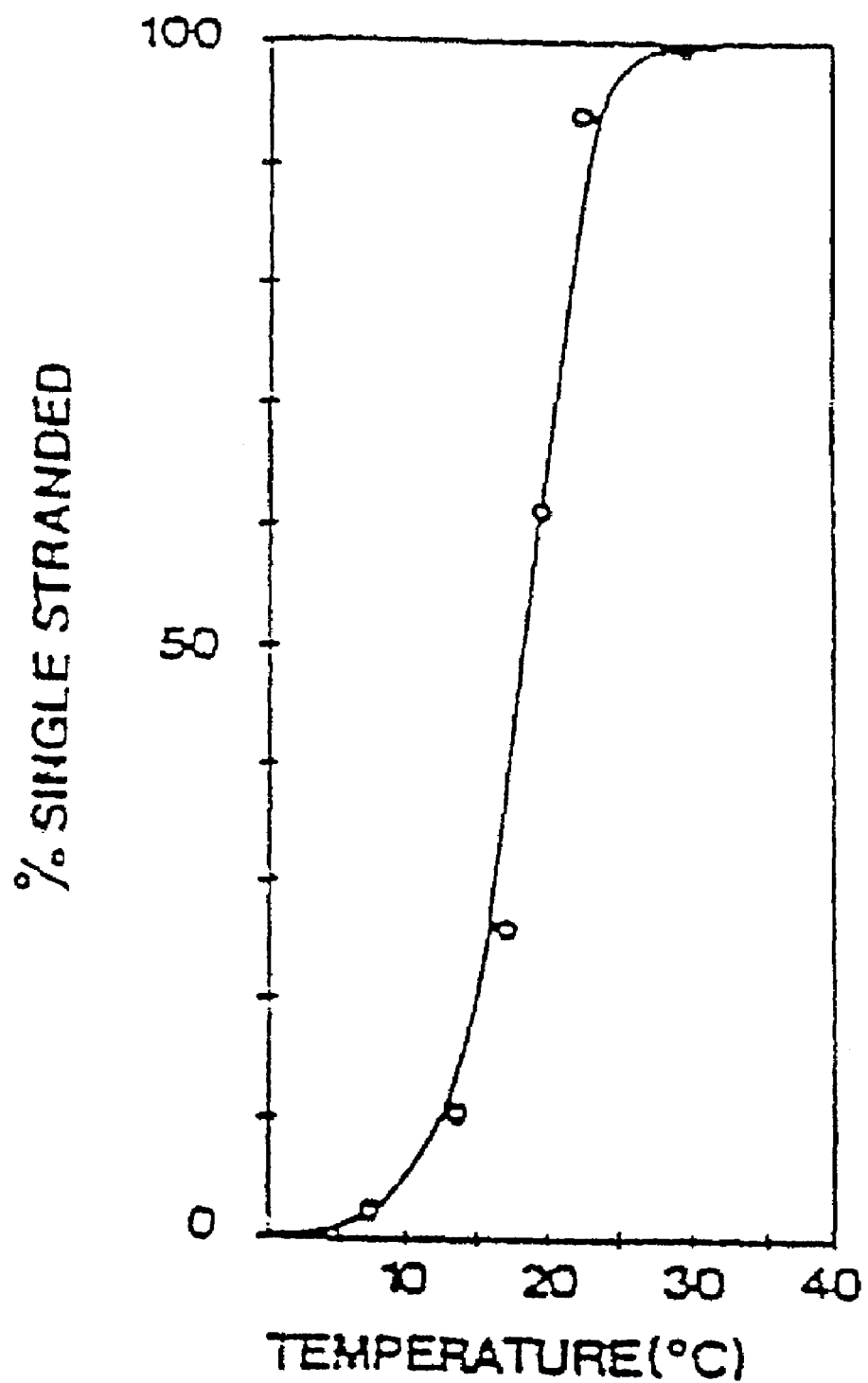

FIG. 3 describes the kinetic stability of a fully matched hybrid obtained with a probe 8 nucleotides in length. Stability is expressed as a fraction of the hybrid dissociated in unit time (minutes) as a function of temperature. 1.4 pmol of NCATGAGCANN as applied to each dot and hybridized with TGCTCATG as probe in a concentration of 4 nM. The equal amounts of hybrid were incubated at the indicated temperatures for a short time in a large volume of buffer and the remaining hybrid measured. Each point represents the average value for four dots. The curve is computer fitted with $E_\alpha$=47.3 Kcal/mol obtained from the experimental points by the least squares method.

FIG. 4 indicates the properties of short oligonucleotide hybridization. In FIG. 4a, non-optimized discrimination with probes 6, 7, and 8 nucleotides in length is illustrated. The probe GCTCAT was hybridized to the target sequence NCATGAGCANN which contains the perfectly matching sequence (underlined). The NNCATGAGTTN target sequence contains an end mismatch (double underlined). 1.4 pM of each target was applied to the filter. The probe GCTCATG, and the probe TGCTCATG were used against 50 ng of IF and M13 DNA. The probe concentration was 4 nM.

In FIG. 4b, limits of signal detection are examined. The indicated volumes of IF culture supernatants of average titer of 6×10$^{11}$ pfu/ml were mixed with an equal volume of 1 M NaOH, 3M NaCl and spotted on a filter as described in a above. Hybridization was at 2° C. with TGCTCATG as the probe.

In FIG. 4c, the time course of hybridization at 13° C. is shown. The IF-M13 system was used with 50 ng of phage DNA per dot, and the probe was TGCTCATG. The 3 hr IF dot contained 18020 cpm measured with 20% efficiency.

Figure 5A:
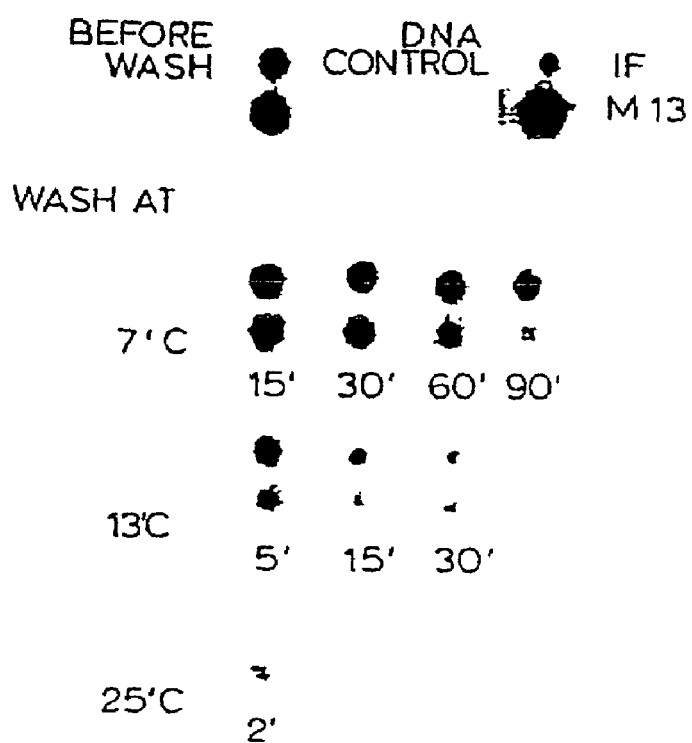
Figure 5B:
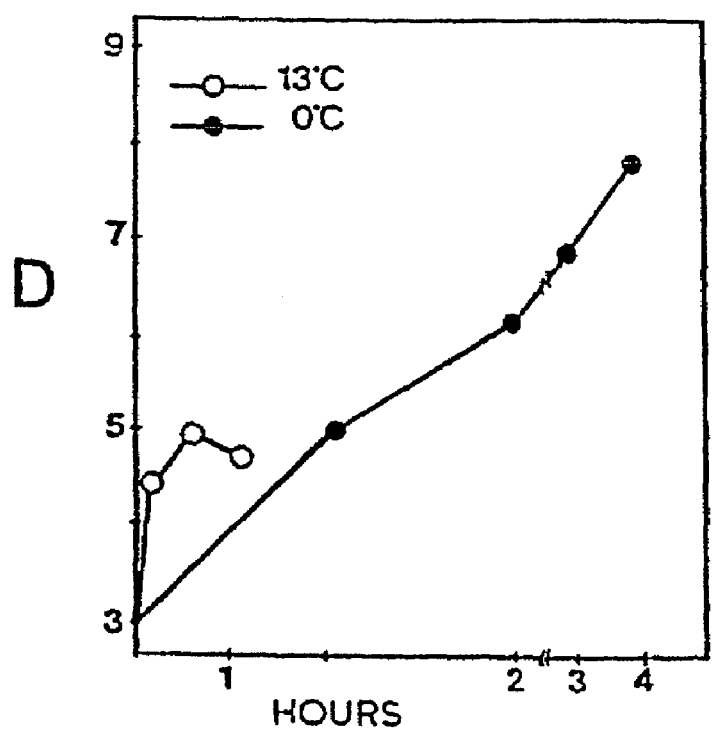

In FIG. 5 the effect of the washing step on discrimination is indicated. In FIG. 5a, inversion of the signal in IF-M13 pair upon washing is shown. 10 ng of IF and 500 ng M13 DNA were applied, and the probe was TGCTCATG. The top row was not washed, the other rows were washed at 7, 13 and 25° C., respectively for the indicated times. A DNA control is included in the top row also. Hybridization with the M13 specific probe AGCTGCTC measures amounts of DNA in the two dots. In FIG. 5b, the change of discrimination with time of washing at 0° C. (full circles) and 13° C. (open circles) is depicted. 100 ng each of IF and M13 were applied to form dots. The dots were hybridized to probe TGCTCATG and probe AGCTGCTC was used in the control DNA hybridization (see top row, on the right, panel a). The dots were then washed at the indicated temperatures. At each time point the pairs of dots were removed and the ratio of radioactivity remaining in the each dot was measured. The D or discrimination was calculated as the mean value of the ratios for the duplicate pairs of dots.

FIG. 6 demonstrates the effects of complexity of target sequences on discrimination. 50 ng each of IF and M13 were hybridized with the indicated probes at a concentration of 4 nM. No wash was performed. The number of matched and end base mismatched targets in IF and M13 is indicated for each probe.

Figure 7C:
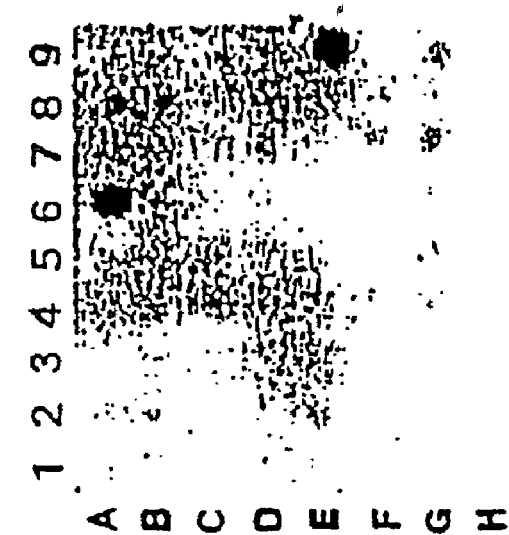
Figure 7B:
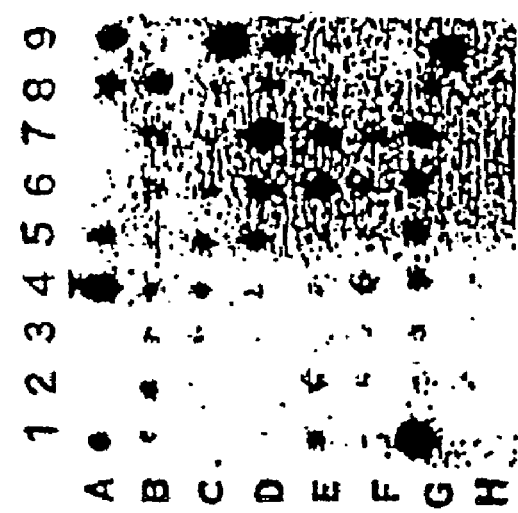
Figure 7A:
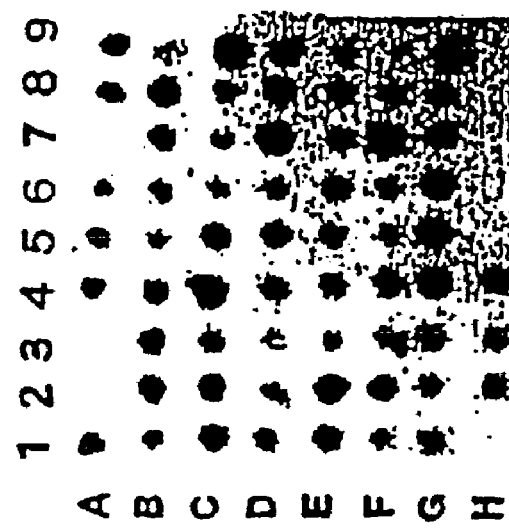

FIG. 7 examines an array of clones for the presence of an oligonucleotide sequence. 51 recombinant plasmid DNAs (10±5 ng) were spotted in rows B to H, columns 1 to 8 (except row H). Line A and column 9 contained control DNAs of known sequence. Unknown clones were taken from human brain cDNA library in Bluescript vector (BS) (Stratogene Cat. No. 935205). Controls of known sequence in lines A1 to A8 and A9 to G9 are: IF(M13), M13, Alu(M13), IF(BS), BS, 1M(pUC 9), pUC 9, 2M(pUC 9), respectively except that in the vertical row Alu(M13) was omitted. 1N and 2H are rat β-globin gene subclones. The probe concentration was 8 nM. In FIG. 7a, BS specific probe CTCCCTTT was also contained in IF and 2M inserts but not in M13 and pUC vectors. In FIG. 7b, the sequence of probe CCAGTTTT was contained in the IF insert but not in either vector. In FIG. 7c, the sequence of probe GCCTTCTC was contained in the 1M insert only.

Figure 8:
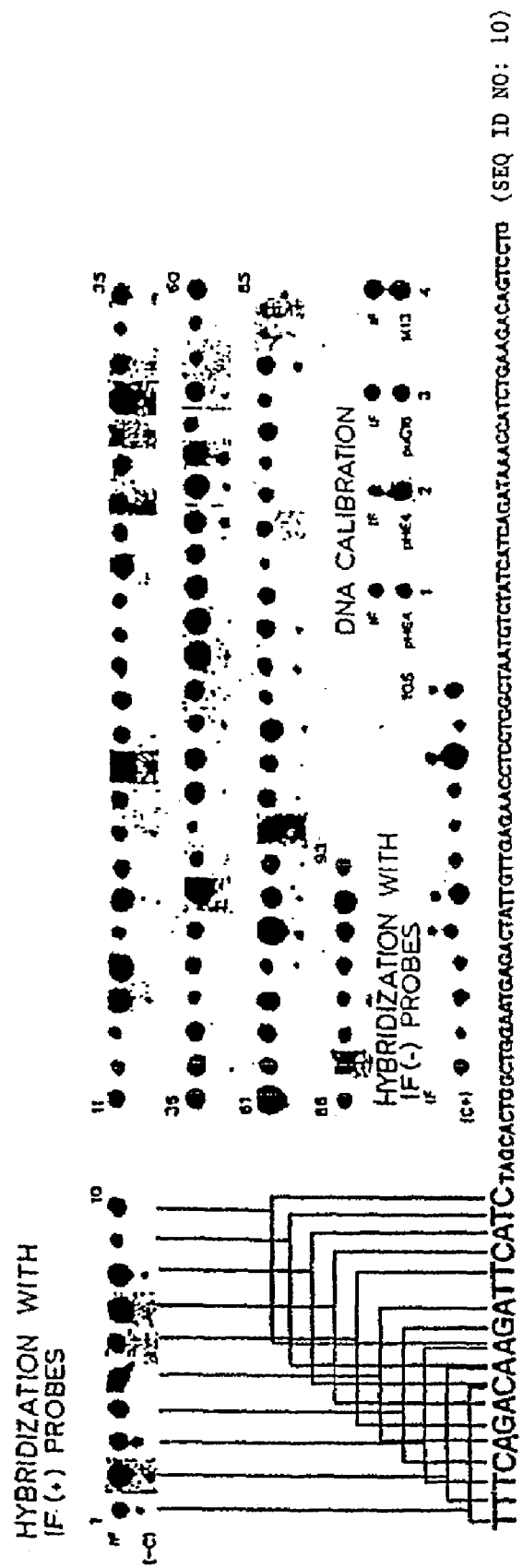

FIG. 8 sequencing 100 bp of 921 bp β$_1$-human interferon gene fragment. (IF) by hybridization.

Part 1. Hybridization results. A. Hybridization with 93 probes (72) octamers and 21 nonamers with the full match in IF. IF and controls rat globin clones pHEA and pHI were PCR amplified while H13 mp18 and pUC18 were in linearized double stranded form. Base denatured DNA (20 ng of IF and equimolar amounts of control DNA) were spotted on Gene Screen membranes (N.E.N.). Hybridization was according to Drmanac et al., described in § 6 below. Briefly, γ-$^{32}$ end labeled probes (3.3 pm, 10 mCI, Amersham 3000 C/mM in concentration of 10 ng/ml were hybridized at 12° C. in 0.5 M Na$_2$HPO$_4$ pH 7.2, 7% Na-lauryl Sarcosine for 3 hours. All probes were made by Genesys, Inc., Houston. Hybrids were washed in 6×SSC at 0° for 40 minutes and autoradiographed for 4–48 hours. Test dot signal intensity, Hp, and discrimination as ratio of signals of test over control dot, D, were visually estimated. For probes 34 and 74, dot radioactivity was measured in a scintillation counter. Hp was 6,000 and 300 cpm, D was 20 and 4, and a film was exposed for 4 and 48 hr respectively. B. Hybridization with 12 probes (11 octamers and 1 nonamer) which have end mismatch in IF fragment. Control DNAs having single full match targets were pHEA for probes 97., 98., 102., pUC18 for 95., 100., 104., 105., and M13 for 94., 96., 99., 101., and 103. Probes 104 and 105 have 3 end-mismatched targets in IF. Hybridization procedures were as described in A. C. DNA Calibration. 1. and 2. IF and pHEA, probe CTGATAT. 3. IF and pUC18 probe CAGATGGT. 4 IF and M13mp18, probe GACTGTCT. The ratios of DNA amounts in IF and control dot were 1:1 in panel 1., 3., 4., and 1:3 in panel 2., respectively. Filters with IF and pH had 1:2 ratio with probe CTGATGAT. Filters show in 2. were used with probes 1., 3., 4., 6. to 8., 10. to 13., containing; pUC18 with probes 31 and 85.: containing M13 with probes 53 and 74; and containing pH with probes 22, 54., 55., 69., 70., 83., and 84. The remainder of probes were used on filters of the type shown on panel 1.

Part 2. 10 bp sequence, position 625–726 in Eco RI $\beta_1$-interferon fragment. The locations of the first 10 probes in the sequence are indicated.

Part 3. List of probes used. The numbers after the probe sequences are ΔH, Hp. and D respectively. ΔH was calculated Hp and D were visually estimated on the basis of the radioactivity measurements of the selected examples ranging from 300–10,000 cpm per dot. Each symbol after the probe indicates the presence of one end mismatched target in its control DNA dot.

FIG. 9 an example of the discriminative hybridization with 8-mers. On each filter the upper dot contains 15 ng of EcoRI-BglII 920 bp genomic fragment with interferon beta-1 gene (IF) and the lower dot contains 25 ng of 1500 bp of rat beta globin gene (GL) prepared by PCR from clones in bluescript vector using universal and reverse sequencing primers. Each probe was hybridized and washed under the same conditions. $^{32}$P labeled probes (by T4-polynucleotide kinase) at a concentration of 4 nM in 0.5 M $Na_2HPO_4$ pH 7.2, 7% Sodium lauroyl sarcosine were hybridized at 12° C. for 3 h. Hybrids were washed in 6×SSC at 2° C. for 40 minutes and autoradiographed for 6 h. Panel on top represents hybridization with probe complementary to amplified vector end and reveals the molar ratio of the two target DNAs. First three 8-mer probes are designed to have perfect target in interferon sequence and target with end mismatch in globin sequence, and probe 4 opposite. Over 5 fold discrimination is obtained with each probe, having 3 to 6 (C+G). In the case of the most stable probe (probe 1) similar discrimination is obtained but both dots are stronger than in case of other probes.

Figure 10:
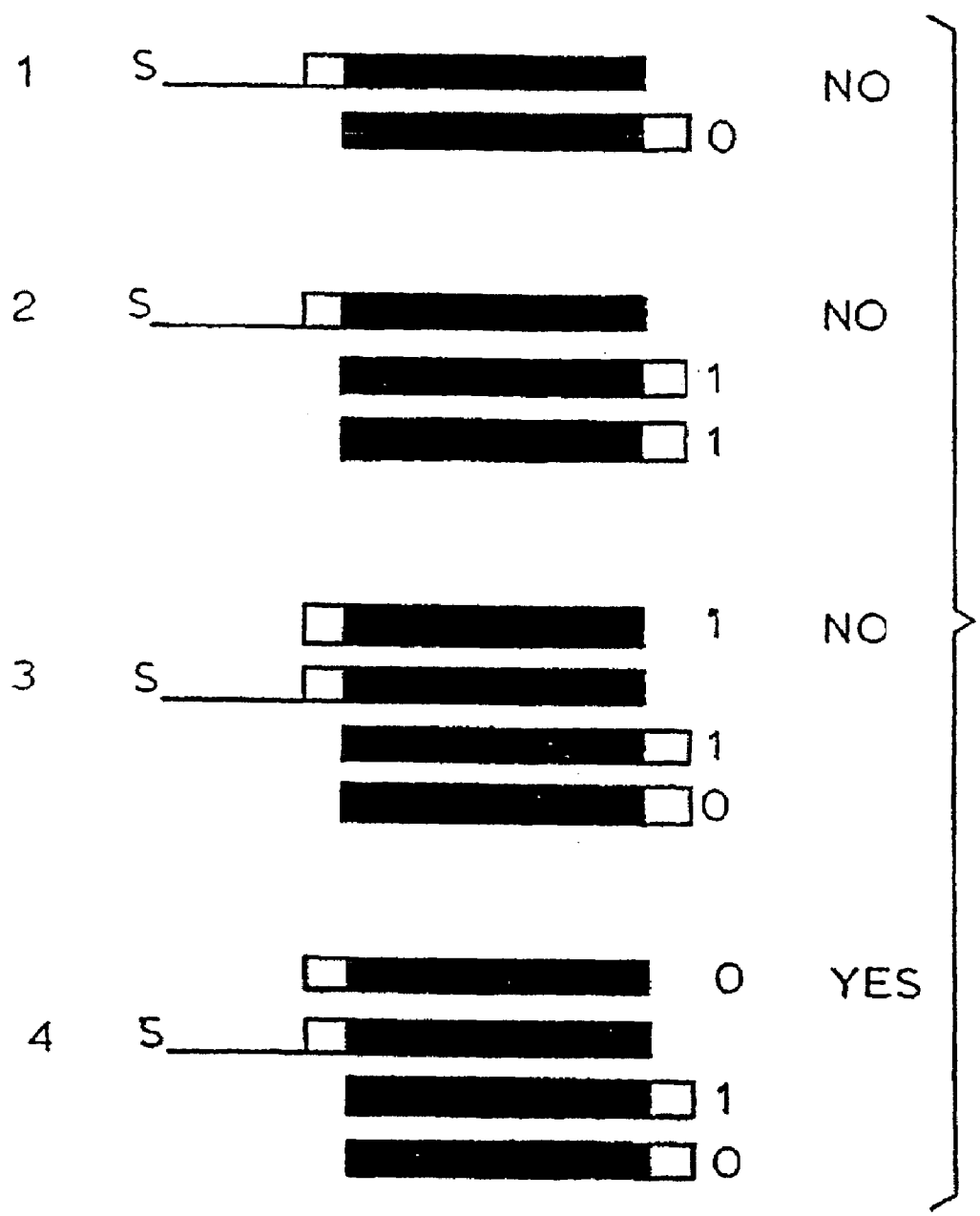

FIG. 10 k-tuple overlap rule. S—start of subfragment assembly. Filled bars—the identical parts of k-tuples. Empty bars—non-identical parts of k-tuples. 0, 1 non occurrence or occurrence, respectively in k-tuple set. (1–3)—situations violating the rule. (4) situation recognized by the overlapping rule.

Figure 11:
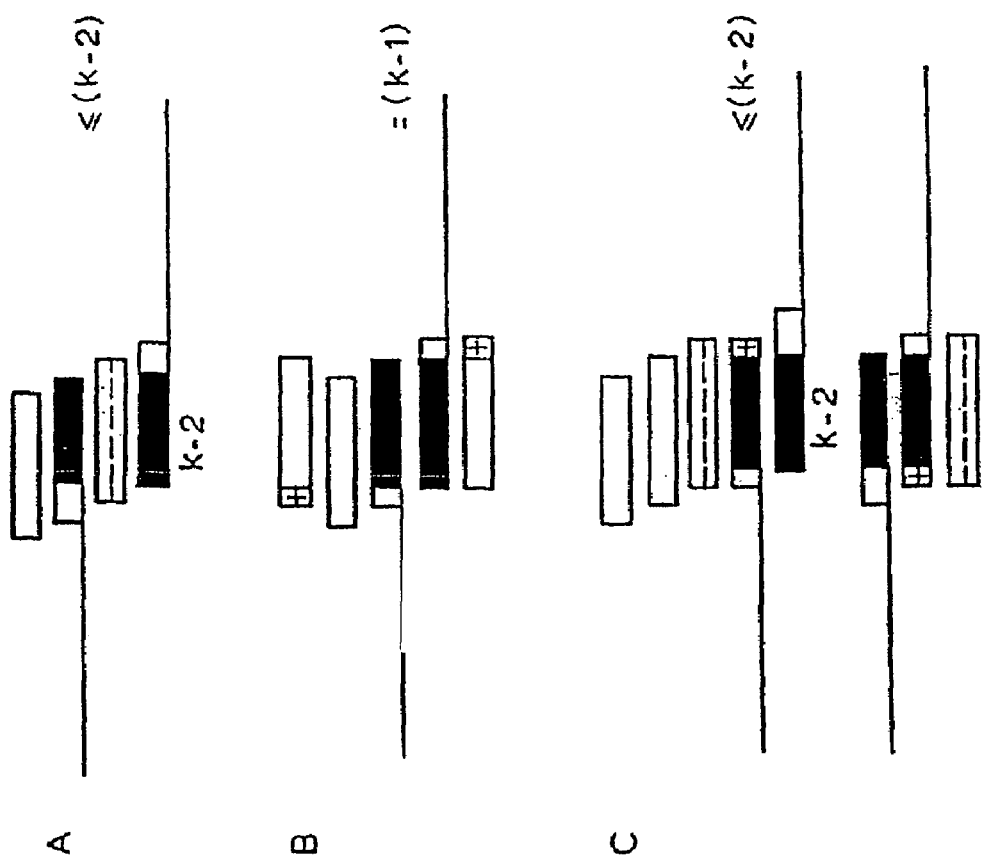
Figure 12A:
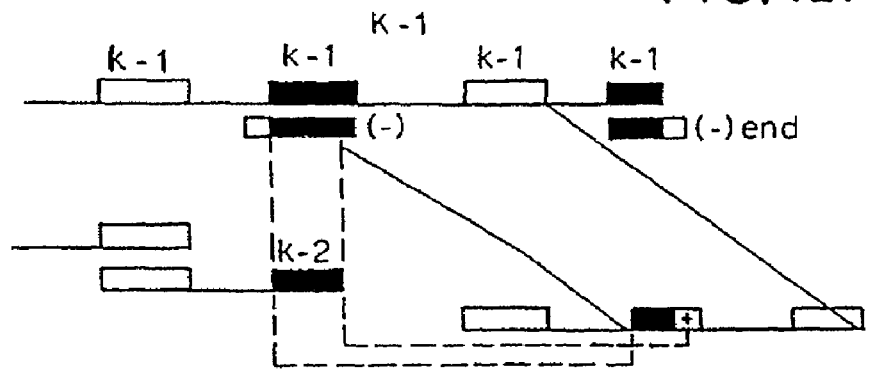
Figure 12B:
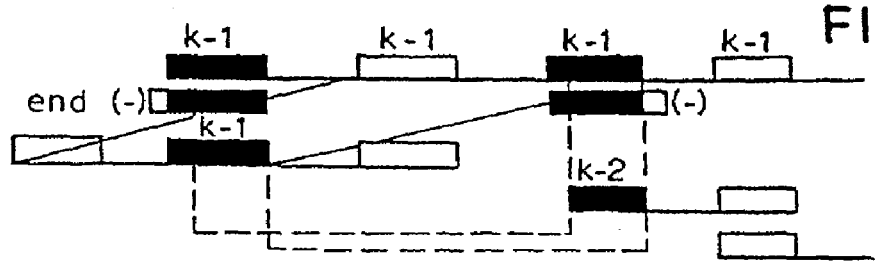
Figure 12C:
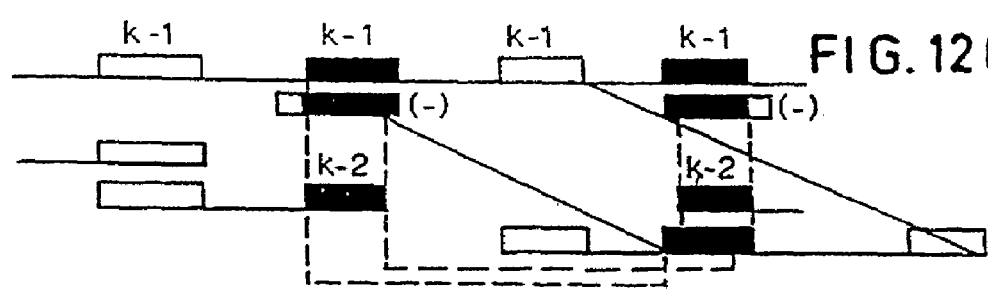
Figure 12D:
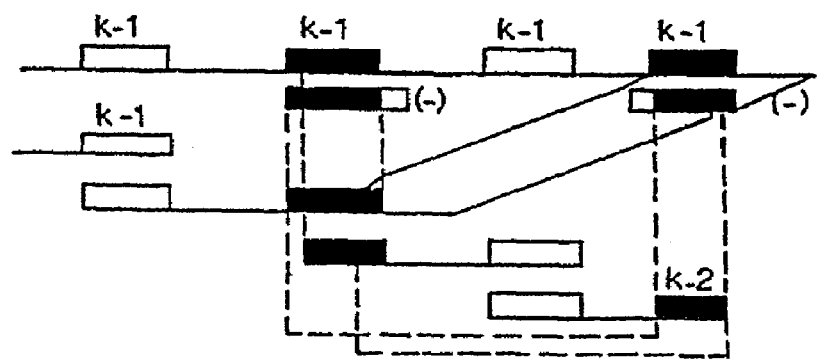
Figure 12E:
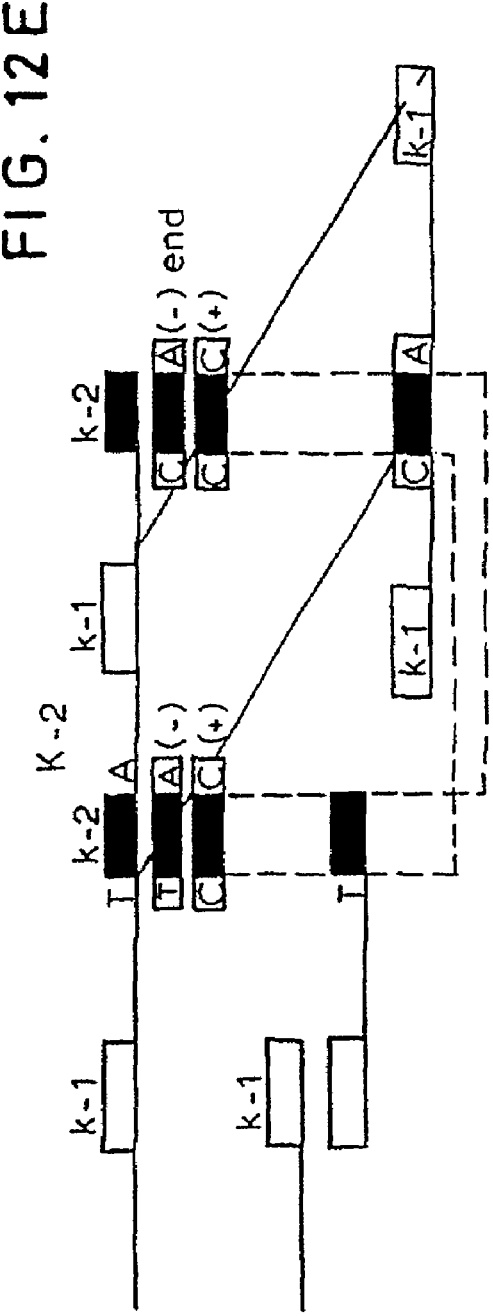
Figure 12F:
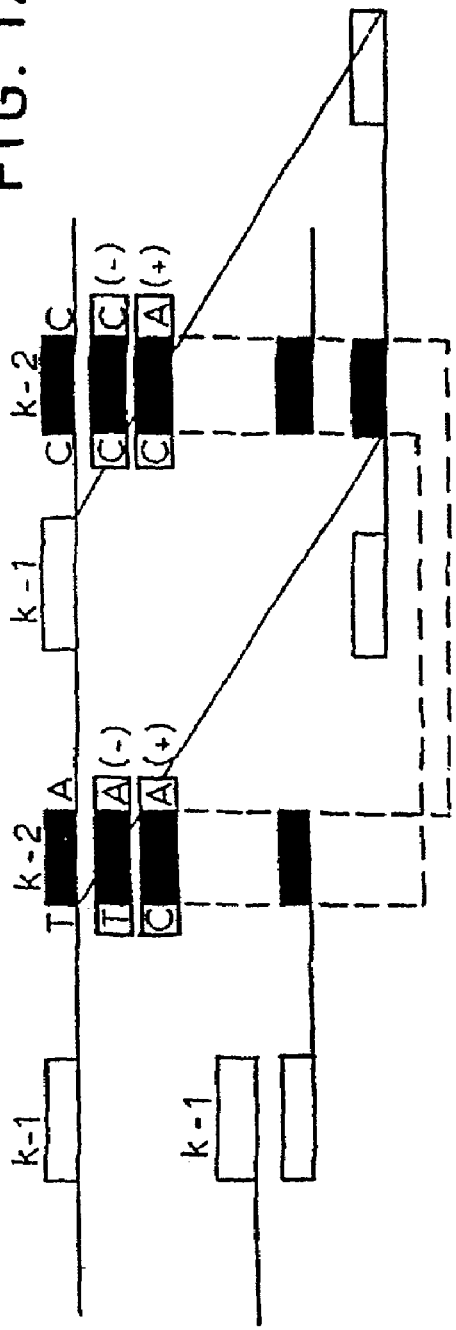

FIG. 11 Examples of generation of short pSFs. Bars are k-tuples. Filled parts of are bars overlapping sequences which length are indicated on the right site. Open bars are correct k-tuples. Bars with dashed line are false negative k-tuples. Bars with (+) are false positive k-tuples; positions of (+) indicate the wrong base. Horizontal lines are extensions of subfragments in the considered site.

FIG. 12 Process of formation of misconnected subfragments. Column I: Misconnection due to the presence of false negative k-tuples in the set. Column II: Misconnection due to the simultaneous presence of both false positive and false negative k-tuples. Top lines-actual sequences. Immediately below-false k-tuples. Lower lines-generated subfragments representing the sequence. Filled bars-overlapping sequences present at the point of misconnection. Open bar-any other repeated sequences. Oblique lines show the wrong position of a part of a sequence within the misconnected subfragment. Dashed line indicate the position in subfragment of sequence used for overlap, causing the misconnection.

5. DETAILED DESCRIPTION OF THE INVENTION

The method of the invention of sequencing by hybridization is based on an entirely different logical principle than previous methods of sequencing which have been described above in § 2.3. Known methods of sequencing define a nucleic acid sequence in a base by base fashion that is read from the position of DNA fragments in polyacrylamide gels where the fragments are produced by base specific chemical degradation or chain termination techniques.

In contrast, the method of sequencing of the present invention is a process comprising hybridizing oligonucleotides to a target sequence, detecting the hybridized oligonucleotides, and assembling the sequence of the target from the sequence of the hybridizing oligonucleotides. The method of sequencing according to the present invention is most suitable for determining the sequence of complex nucleic acid fragments, molecules, or genomes and especially those containing one million or more nucleotide base pairs.

According to the method of the invention, the number of oligonucleotide probes, the lengths and types of target nucleic acid sequences, the numbers of subfragments of the target nucleic acid sequences and the numbers of hybridizations necessary for sequencing have been calculated and show that sequencing by hybridization is more efficient than sequencing by traditional methods.

5.1. Oligonucleotide Probes and Targets Suitable for SBH

A mismatch-free hybridization of oligonucleotides to an unknown target nucleic acid represents, in essence, a sequencing of complementary target. Probability calculations and, in part, computer simulations estimate the types and numbers of oligonucleotides that would have to be synthesized in order to sequence a megabase plus segment of DNA.

In order to obtain the required amount of experimental data defined as a matrix of (number of fragments-clones)× (number of probes), the number of probes can be reduced depending on the number of fragments used and vice versa. The optimal ratio of the two numbers is defined by the technological requirements of a particular sequencing by hybridization process. The useful probes are those longer than 6 bases, since the shorter ones would require use of unsuitable and unpractical nucleic acid fragments shorter than a few hundred bases long.

There are two parameters which influence the choice of probe length. The first is the success in obtaining hybridization results that show the required degree of discrimination. The second is the technological feasibility of synthesis of the required number of probes.

The requirement of obtaining sufficient hybridization discrimination with practical and useful amounts of target nucleic acid limits the probe length from both sides. It is difficult to obtain a sufficient amount of hybrid with short probes, and to discriminate end mismatch with long probes. There is no evidence for use of probes shorter than 11-mers in the literature, except for very stable ones [Estivill et al., Nucl. Acids Res. 15: 1415 (1987)]. On the other hand, probes longer than 15 bases discriminate end mismatch with difficulty [Wood et al., Proc. Nat'l. Acad. Sci. USA 82: 1585 (1985)].

One solution for the problem of unstable probes and end mismatch discrimination is the use of a group of longer probes representing a single shorter probe in an informational sense. Groups of sixty-four 11-mers can be used instead of single 8-mers. Every member of the group has a common, core 8-mer and one of three possible variations on outer positions with two variations at each end. The probe can be represented as 5'(A,T,C,G)(A,T,C,G)N8(A,T,C,G) 3'. With this type of probe one does not need to discriminate the non-informative end bases (two on 5' end, and one on 3' end) since only the internal 8-mer is read. This solution requires the use of higher mass amounts of probes and label in hybridization reactions.

These disadvantages are eliminated by the use of a single condition of discriminative hybridization for oligomer probes as short as 6-mers (see Examples 6.3 and 6.4). The length of probes are restricted by the technological problem of having a practical number of probes that can be synthesized and utilized. At this time it may be difficult for some to synthesize more than about 100,000 8-mer and some additional 9-mer probes or groups of 11-mers of types 5'(A,T,C,G)(A,T,C,G)N8(A,T,C,G)3' and 5'(A,T,C,G)N9(A,T,C,G)3' by the current methods for synthesis of individual oligonucleotides.

The number of hybridization reactions is dependent on the number of discrete labeled probes. Therefore in the cases of sequencing shorter nucleic acids using a smaller number of fragments-clones than the number of oligonucleotides, it is better to use oligomers as the target and nucleic acid fragments as probes. For example, one needs 20,000 clones and up to five fold more oligonucleotides (50–100,000) to sequence 10 million bp of DNA with 8-mer oligonucleotides.

Target nucleic acids which have undefined sequences can be produced as a mixture of representative libraries in a phage or plasmid vector having inserts of genomic fragments of different sizes or in samples prepared by PCR. Inevitable gaps and uncertainties in alignment of sequenced fragments arise from nonrandom or repetitive sequence organization of complex genomes and difficulties in cloning "poisonous" sequences in *Escherichia coli*. These problems are inherent in sequencing large complex molecules using any method. In this invention such problems are minimized by the choice of libraries and number of subclones used for hybridization. Alternatively such difficulties can be overcome through the use of amplified target sequences, e.g. by PCR amplification, ligation-amplified reactions etc. Because this invention is based on simple biochemical procedures, the method of the invention is inherently easier to automate than existing sequencing methods. The sequence can be derived from simple primary data using only extensive computing.

5.2. Determining Sequence from the Oligonucleotide Hybridization Data

Sequencing by hybridization (SBH) of a target nucleic acid can be visualized as consisting of two steps; 1) a process of dissolving the target nucleic acid into all its constituent oligonucleotide N-mers, and 2) the back assembly of N-mers detected by hybridization and assembled by overlap into an extended sequence. In the invention, hybridization of all possible N-mer oligonucleotide probes to the target nucleic acid determines the N-mer oligonucleotide subset contained in the primary sequence of the target nucleic acid and is the first step in the process of the invention. As indicated in FIG. 1 a nucleic acid fragment can be dissolved into all constituent oligonucleotides. Positively hybridizing N-mer oligonucleotide probes are ordered and the sequence of the target DNA is determined using (N−1) mer overlapping frames between the oligonucleotide probes.

Reassembling the sequence of known oligonucleotides that hybridize to the target nucleic acid to generate the sequence of the target nucleic acid cannot be accomplished in some cases. This is because some information is lost if the target nucleic acid is not in fragments of appropriate size (see FIG. 2) in relation to the size of oligonucleotide that is used for hybridizing. The quantity of information lost is proportional to the length of a target being sequenced. However, if sufficiently short targets are used, their sequence can be unambiguously determined.

The sequence assembly will be interrupted where ever a given overlapping (N−1)mer is duplicated two or more times. Then either of the two N-mers differing in the last nucleotide can be used in extending the sequence. This branching point limits unambiguous assembly of sequence.

The probable frequency of duplicated sequences that would interfere with sequence assembly which is distributed along a certain length of DNA can be calculated. This derivation requires the introduction of the definition of a parameter having to do with sequence organization: the sequence subfragment (SF). A sequence subfragment results if any part of the sequence of a target nucleic acid starts and ends with an (N−1)mer that is repeated two or more times within the target sequence. Thus, subfragments are sequences generated between two points of branching in the process of assembly of the sequences in the method of the invention. The sum of all subfragments is longer than the actual target nucleic acid because of overlapping short ends. Generally, subfragments cannot be assembled in a linear order without additional information since they have shared (N−1)mers at their ends and starts. Different numbers of subfragments are obtained for each nucleic acid target depending on the number of its repeated (N−1)mers. The number depends on the value of N−1 and the length of the target.

Probability calculations can estimate the interrelationship of the two factors which are given in graphical form in FIG. 2. If the ordering of positive N-mers is accomplished by using overlapping sequences of length N−1 or at in average distance of $A_o$, the N−1 of a fragment $L_f$ bases long is given by equation one:

$$Nsf-1+A_o \times \Sigma K \times P(K, L_f)$$

where K greater than or −2, and $P(K, L_f)$ represents the probability of an R-mer occurring K-times on a fragment $L_f$ base long. Also, a computer program that is able to form subfragments from the content of N-mers for any given sequence is described below in Appendix A.

As shown (FIG. 2) the number of subfragments increases with the increase of lengths of fragments for a given length of probe. Obtained subfragments may not be uniquely ordered among themselves. Although not complete, this information is very useful for comparative sequence analysis and the recognition of functional sequence characteristics. This type of information we call partial sequence. Another way of obtaining partial sequence is the use of only a subset of oligonucleotide probes of a given length.

There is a relatively good agreement between predicted sequence according to theory and a computer simulation for a random DNA sequence. For instance, for N−1=7, [using an 8-mer or groups of sixty-four 11-mers of type 5'(A,T,C,G)(A,T,C,G)N8(A,T,C,G)3'] a target nucleic acid of 200 bases will have an average of three subfragments. However, because of the dispersion around the mean, a library of target nucleic acid should have inserts of 500 bp so that less than 1 in 2000 targets have more than three subfragments. Thus in an ideal case of sequence determination of a long nucleic acid of random sequence, it is only necessary to use a representative library with sufficiently short inserts of target nucleic acid. For such inserts it is possible to reconstruct the individual target by the method of the invention. The entire sequence of a large nucleic acid is then obtained by overlapping of the defined individual insert sequences.

We found a solution to reduce the need for very short fragments, e.g. 50 bases for 8-mer probes. The basis for the use of longer fragments lies in the use of information contained in the overlapped fragments present in every random DNA fragmentation process like cloning, or random PCR. It is also possible to use pools of short physical nucleic acid fragments. Using 8-mers or 11-mers like 5'(A,T,C,G)(A,T,C,G)N8(A,T,C,G)3' for sequencing 1 megabase, instead of needing 20,000 50 bp fragments only 2,100 samples are sufficient. This number consists of 700 random 7 kb clones (basic library), 1250 pools of 20 clones of 500 bp (subfragments ordering library) and 150 clones from jumping (or similar) library. The developed algorithm (see Appendix) can regenerate sequence using hybridization data of these described samples.

6. EXAMPLE: MATERIALS AND METHODS

6.1. Materials

Oligonucleotides were either purchased from Genetic Designs, Inc. Houston, Texas or made on an Applied Biosystems 381A DNA synthesizer. Most of the probes used were not purified by HPLC or gel electrophoresis. Probes were designed to have both a single perfectly complementary target in IF, a M13 clone containing a 921 bp Eco RI-Bgl II human $\beta_1$-interferon fragment [Ohno and Tangiuchi, Proc. Natl. Acad. Sci. 74: 4370–4374 (1981)], and at least one target with an end base mismatch in M13 vector itself.

6.2. Oligonucleotide Labeling

End labeling of oligonucleotides was performed as described [Maniatis et al., in Molecular Cloning: a Laboratory Manual, Cold Spring Harbor Laboratory, Cold Spring Harbor, N.Y. (1982)] in 10 µl containing $T_4$-polynucleotide kinase (5 units Amersham), $\gamma$-$^{32}$P-ATP (3.3 pM, 10 µCi Amersham 3000 Ci/mM) and oligonucleotide (4 pM, 10 ng). Specific activities of the probes were 2.5–5×10$^9$ cpm/nM.

6.3. Hybridization Procedures

Single stranded DNA (2 to 4 µl in 0.5 NaOH, 1.5 M NaCl) was spotted on a Gene Screen membrane wetted with the same solution, the filters were neutralized in 0.05 M $Na_2HPO_4$ pH 6.5, baked in an oven at 80° C. for 60 min and UV irradiated for 1 min. Then, the filters were incubated in hybridization solution (0.5 M $Na_2HPO_4$ pH 7.2, 7% sodium lauroyl sarcosine for 5 min. at room temperature and placed on the surface of a plastic Petri dish. A drop of hybridization solution (10 µl, 0.5 M $Na_2HPO_4$ pH 7.2, 7% sodium lauroyl sarcosine) with a $^{32}$P end labeled oligomer probe at 4 nM concentration was placed over 1–6 dots, overlayed with a square piece of polyethylene (approximately 1×1 cm), and incubated in a moist chamber at the indicated temperatures for 3 hr. Hybridization was stopped by placing the filter in 6×SSC washing solution for 3×5 minute at 0° C. to remove unhybridized probe. The filter was either dried, or further washed for the indicated times and temperatures, and autoradiographed. For discrimination measurements, the dots were excised from the dried filters after autoradiography, placed in liquid scintillation cocktail and counted. The uncorrected ratio of cpms for IF and M13 dots is given as D.

6.4. EXAMPLE: VERY SHORT OLIGONUCLEOTIDE HYBRIDIZATION

The conditions reported herein allow very short oligonucleotide hybridization but ensure discriminations between matched and mismatched oligonucleotides that are complementary to and therefore bind to a target nucleic acid. Factors which influence the efficient detection of hybridization of specific short sequences based on the degree of discrimination (D) between a perfectly complementary target and an imperfectly complementary target with a single mismatch in the hybrid are defined. Experimental tests used dot blot hybridization of twenty-eight probes that were 6 to 8 nucleotides in length to two M13 clones or to model oligonucleotides bound to membrane filters. The principles guiding the experimental procedures are given below.

6.5. Theoretical Principles

Oligonucleotide hybridization to filter bound target nucleic acids only a few nucleotides longer than the probe in conditions of probe excess is a pseudo-first order reaction with respect to target concentration. This reaction is defined by equation two:

$$S_t/S_o = e^{-K_h \, OP \, T}$$

$S_t$ and $S_o$ are target sequence concentrations at time t and $t_o$, respectively. (OP) is probe concentration. The rate constant for hybrid formation, $k_h$, increases only slightly in the 0° C. to 30° C. range [Porschke and Eigen, J. Mol. Biol. 62: 361 (1971); Craig et al., J. Mol. Biol. 62: 383 (1971)]. Hybrid melting is a first order reaction with respect to hybrid concentration (here replaced by mass due to filter bound state) as shown in equation three:

$$H_t/H_o = e^{-k_m t}$$

In equation three, $H_t$ and $H_o$ are hybrid concentrations at times t and $t_o$, respectively; $k_m$ is a rate constant for hybrid melting which is dependant on temperature and salt concentration [Ikuta et al., Nucl. Acids Res. 15: 797 (1987); Porschke and Eigen, J. Mol. Biol. 62: 361 (1971); Craig et al., J. Mol. Biol. 62: 383 (1971)]. During hybridization, which is a strand association process, the back melting, or strand dissociation, reaction takes place as well. Thus, the amount of hybrid formed in time t is a result of forward and back reactions. The equilibrium can be moved towards hybrid formation by increasing probe concentration and/or decreasing temperature. However, during washing cycles in large volumes of buffer, the melting reaction is dominant and the back reaction of hybridization is insignificant, since the probe is absent. This analysis indicates workable short oligonucleotide hybridization (SOH) conditions can be varied for probe concentration or temperature.

D or discrimination is defined in equation four:

$$D = H_p(t_w)/H_i(t_w)$$

$H_p(t_w)$ and $H_i(t_w)$ are the amounts of hybrids remaining after a washing time, $t_w$, for the identical amounts of perfectly and imperfectly complementary duplex, respectively. For a given temperature, the discrimination D changes with the length of washing time and reaches the maximal value when $H_i = B$ which is equation five.

The background, B, represents the lowest hybridization signal detectable in the system. Since any further decrease of $H_i$ cannot be examined, D would increase upon continued washing. Washing past $t_w$ just decreases $H_p$ relative to B, and is seen as a decrease in D. The optimal washing time, $t_w$, for imperfect hybrids, from equation three and equation five is Equation six:

$$t_w = -\ln(B/H_i(t_o))/K_{m,i}$$

Since $H_p$ is being washed for the same $t_w$, combining Equation three for $H_p$, Equation four and Equation six, one obtains the optimal discrimination function in Equation seven:

$$D = e \ln(B/H_i(t_o)) k_{m,p}/k_{m,i} \times H_p(t_o)/B$$

The change of D as a function of T is important because of the choice of an optimal washing temperature. It is obtained by substituting the Arhenius equation which is Equation eight:

$$K = A e^{-E_\alpha/RT}$$

into Equation seven. The final equation is Equation nine:

$$D = H_p(t_o)/B \times (B/H_i(t_o))^{(A_p/A_i)} e^{(E_{\alpha,i} - E_{\alpha,p})/RT};$$

B less than $H_i(t_o)$.

Since the activation energy for perfect hybrids, $E_{\alpha,p}$, and the activation energy for imperfect hybrids, $E_{\alpha,i}$, can be either equal, or $E_{\alpha,i}$ less than $E_{\alpha,p}$, D is temperature independent, or decreases with increasing temperature, respectively. This result implies that the search for stringent temperature conditions for good discrimination in SOH is unjustified. By washing at lower temperatures, one obtains equal or better discrimination, but the time of washing exponentially increases with the decrease of temperature, as can be seen by substituting Equation eight in Equation six. A further property of Equation nine for $E_{\alpha,i}$ less than $E_{\alpha,p}$, is that discrimination more strongly decreases with T, if $H_i(t_o)$ increases relative to $H_p(t_o)$.

Finally, the analysis of Equation nine shows that D at lower temperatures depends to a higher degree on the $H_p(t_o)/B$ ratio than on the $H_p(t_o)/H_i(t_o)$ ratio. This result indicates that it is better to obtain a sufficient quantity of $H_p$ in the hybridization regardless of the discrimination that can be achieved in this step. Better discrimination can then be obtained by washing, since the higher amounts of perfect hybrid allow more time for differential melting to show an effect. Similarly, using larger amounts of target nucleic acid a necessary discrimination can be obtained even with small differences between $K_{m,p}$ and $K_{m,i}$.

Extrapolated to a more complex situation than covered in this simple model, the result is that washing at lower temperatures is even more important for obtaining discrimination in the case of hybridization of a probe having many end-mismatches within a given nucleic acid target.

6.6. Experimental Parameters

Using the described theoretical principles as a guide for experiments, reliable hybridizations have been obtained with probes six to eight nucleotides in length. All experiments were performed with a floating plastic sheet providing a film of hybridization solution above the filter. This procedure allows maximal reduction in the amount of probe, and thus reduced label costs in dot blot hybridizations. The high concentration of sodium lauroyl sarcosine instead of sodium lauroyl sulfate in the phosphate hybridization buffer allows dropping the reaction from room temperature down to 12° C. Similarly, the 4–6×SSC, 10% sodium lauroyl sarcosine buffer allows hybridization at temperatures as low as 2° C. The detergent in these buffers is essential for obtaining tolerable background with up to 40 nM concentrations of labeled probe. Preliminary characterization of the thermal stability of short oligonucleotide hybrids was determined on a prototype octamer with 50% GC content, i.e. probe of sequence TGCTCATG. The theoretical expectation is that this probe is among the less stable octamers. Its transition enthalpy is similar to those of more stable heptamers or, even to probes 6 nucleotides in length [Bresslauer et al., Proc. Natl. Acad. Sci. U.S.A. 83: 3746 (1986)]. The stability of the 8 bp oligonucleotide duplex hybrid as a function of temperature is shown in FIG. 3. Parameter $T_d$, the temperature at which 50% of the hybrid is melted in unit time of a minute is 18° C. The result shows that $T_d$ is 15° C. lower for the 8 bp hybrid than for an 11 bp duplex [Wallace et al., Nucleic Acids Res. 6: 3543 (1979)].

In addition to experiments with model oligonucleotides, an M13 vector was chosen as a system for a practical demonstration of short oligonucleotide hybridization. The main aim was to show useful end-mismatch discrimination with a target similar to the ones which will be used in various applications of the method of the invention. Oligonucleotide probes for the M13 model were chosen in such a way that the M13 vector itself contains the end mismatched base. Vector IF, an M13 recombinant containing a 921 bp human interferon gene insert, carries a single perfectly matched target. Thus, IF has either the identical or a higher number of mismatched targets in comparison to the M13 vector itself.

Using low temperature conditions and dot blots, sufficient differences in hybridization signals were obtained between the dot containing the perfect and the mismatched targets and the dot containing the mismatched targets only. This was true for the 6 nucleotides long oligonucleotides and was also true for the 7 and 8 nucleotide long oligonucleotides hybridized to the large IF-M13 pair of nucleic acids (FIG. 4A).

The hybridization signal depends on the amount of target available on the filter for reaction with the probe. A necessary control is to show that the difference in signal intensity is not a reflection of varying amounts of nucleic acid in the two dots. Hybridization with a probe that has the same number and kind of targets in both IF and M13 shows that there is an equal amount of DNA in the dots (FIG. 4A). Since the efficiency of hybrid formation increases with hybrid length, the signal for a duplex having six nucleotides was best detected with a high mass of oligonucleotide target bound to the filter (FIG. 4A). Due to their lower molecular weight, a larger number of oligonucleotide target molecules can be bound to a given surface area when compared to large molecules of nucleic acid that serves as target.

To measure the sensitivity of detection with unpurified DNA, various amounts of phage supernatants were spotted on the filter and hybridized with a $^{32}$P-labeled octamer. As little as 50 million unpurified phage containing no more than 0.5 ng of DNA gave a detectable signal (FIG. 4B) indicating that sensitivity of the short oligonucleotide hybridization method is sufficient. Reaction time is short, adding to the practicality. For instance, the time of hybridization at 15° C. with 4 nM probe is 3 hours, after which equilibrium is reached (FIG. 4C).

As mentioned in the theoretical section above, the equilibrium yield of hybrid depends on probe concentration and/or temperature of reaction. For instance, the signal level for the same amount of target with 4 nM octamer at 13° C. is 3 times lower than with a probe concentration of 40 nM, and is decreased 4.5 times by raising the hybridization temperature to 25° C.

The utility of the low temperature wash for achieving maximal discrimination is demonstrated in FIG. 5. To make the phenomenon visually obvious, 50 times more DNA was put in the M13 dot than in the IF dot as shown using hybridization with a vector specific probe (FIG. 5 DNA control). In this way, the signal after the hybridization step with the actual probe was made stronger in the mismatched than in the matched case. The $H_p/H_t$ ratio was 1:4. Inversion of signal intensities after prolonged washing at 7° C. was achieved without a massive loss of perfect hybrid, resulting in a ratio of 2:1 (FIG. 5). In contrast, it is impossible to achieve any discrimination at 25° C., since the matched target signal is already brought down to the background level with 2 minute washing; at the same time, the signal from the mismatched hybrid is still detectable. The loss of discrimination at 13° C. compared to 7° C. is not so great but is clearly visible. If one considers the 90 minute point at 7° C. and the 15 minute point at 13° C. when the mismatched hybrid signal is near the background level, which represents optimal washing times for the respective conditions, it is obvious that the amount of matched hybrid is several times greater at 7° C. than at 13° C. To illustrate this further, the time course of the change in discrimination with washing of the same amount of starting hybrid at the two temperatures shows the higher maximal D at the lower temperature (FIG. 5b). These results confirm the trend in the change of D with temperature and the ratio of amounts of the two types of hybrids at the start of the washing step predicted by Equation five.

In order to show the general utility of the short oligonucleotide hybridization conditions, we have looked at hybridization of 4 heptamers, 10 octamers and an additional 14 probes up to 12 nucleotides in length in our simple M13 system. These include the nonamer GTTTTTTAA and octamer GGCAGGCG representing the two extremes of GC content. Although GC content and sequence are expected to influence the stability of short hybrids [Bresslauer et al., Proc. Natl. Acad. Sci. U.S.A. 83: 3746 (1986)], the low temperature short oligonucleotide conditions were applicable to all tested probes in achieving sufficent discrimination. Since the best discrimination value obtained with probes 8 nucleotides in length was 20, a several fold drop due to sequence variation is easily tolerated.

The M13 system has the advantage of showing the effects of target DNA complexity on the levels of discrimination. FIG. 6 shows the discrimination levels prior to washing for several probes with the IF-M13 system. The number of mismatched targets present in the insert and M13 vector are also shown. The general trend of a decrease in measured discrimination with the number of end-mismatched targets is obvious. Thus for two octamers having either none or five mismatched targets and differing in only one GC pair the observed discriminations were 18.3 and 1.7, respectively (FIG. 6).

In order to show the utility of this method, three probes 8 nucleotides in length were tested on a collection of 51 plasmid DNA dots made from a library in Bluescript vector (FIG. 7). One probe was present and specific for Bluescript vector but was absent in M13, while the other two probes had targets that were inserts of known sequence. This system allowed the use of hybridization negative or positive control DNAs with each probe. FIG. 7a shows the variation in dots from sample to sample, since the differences in hybridization with the vector specific probe should reflect the differences in DNA concentration from dot to dot. This probe sequence (CTCCCTTT) also has a complementary target in the interferon insert. Since the M13 dot (A2 FIG. 7a) is negative while the interferon insert in either M13 or Bluescript (A1 and A4, respectively, FIG. 7a) is positive, the hybridization is sequence specific. Similarly, probes that detect the target sequence in only one of 51 inserts (FIG. 7b), or in none of the examined inserts (FIG. 7c) are shown along with controls that confirm that hybridization would have ocurred if the appropriate targets were present in the clones. In scoring positive hybridization, comparison of signal intensities was accomplished not between dots on the same panel, but comparisons were also made for the same dot on panels b and c with the dot on panel a in order to correct for differences in DNA amounts in the dots and, in the case of controls, in complexity.

6.7. Discussion

Thermal stability curves for very short oligonucleotide hybrids that are 6–8 nucleotides in length are at least 15° C. lower than for hybrids 11–12 nucleotides in length [FIG. 1 and Wallace et al., Nucleic Acids Res. 6: 3543–3557 (1979)]. However, performing the hybridization reaction at a low temperature and with a very practical 4–40 nM concentration of oligonucleotide probe allows the detection of complementary sequence in a known or unknown nucleic acid target. To determine an unknown nucleic acid sequence completely, an entire set containing 65,535 8-mer probes can be used. Sufficient amounts of nucleic acid for this purpose are present in convenient biological samples such as a few microliters of M13 culture, a plasmid prep from 10 µl of bacterial culture or a single colony of bacteria, or less than 1 µl of a standard PCR reaction.

Short oligonucleotides 6–10 nucleotides long give excellent discrimination. The relative decrease in hybrid stability with a single end mismatch is greater than for longer probes. Our results with the octamer TGCTCATG (FIG. 5) support this conclusion. In the experiments illustrated in FIG. 5, the target-with a G/T end mismatch is discriminated. The hybridization to the target of this type of mismatch is the most stable of all other types of mismatches which occur in more internal positions of an oligonucleotide. The discrimination achieved is the same as or greater than an internal G/T mismatch in a 19 base paired duplex [Ikuta et al., Nucl. Acids Res. 15: 797 (1987)]. Exploiting these discrimination properties using the described hybridization conditions for short oligonucleotide hybridization allows a very precise determination of oligonucleotide targets in an unknown sequence.

In contrast to the ease of detecting discrimination between perfect and imperfect hybrids, a problem that may exist with using very short oligonucleotides is the preparation of sufficient amounts of hybrids. In practice, the need to discriminate $H_p$ and $H_i$ is aided by increasing the amount of DNA in the dot and/or the probe concentration, or by decreasing the hybridization temperature. However, higher probe concentrations usually increases background. Moreover, there are limits to the amounts of target nucleic acid that are practical to use. This problem was solved by the high concentration of the detergent Sarcosyl in our experiments which gave an effective background with 4 nM of probe. Further improvements can be effected either in the use of competitors for unspecific binding of probe to filter, or by changing the hybridization support material as will be recognized by the skilled artisan. Moreover, for probes having $E_\alpha$ less than 45 Kcal/mol (e.g. for many heptamers and a majority of hexamers modified oligonucleotides give a more stable hybrid [Asseline, et al., Proc. Natl. Acad. Sci. 81: 3297 (1984)] than their unmodified counterparts.

The hybridization conditions described in this invention for short oligonucleotide hybridization using low temperatures give better discrimination for all sequences and duplex hybrid inputs. The only price paid in achieving uniformity in hybridization conditions for different sequences is an increase in washing time from minutes to up to 24 hours depending on the sequence. Moreover, the washing time can be further reduced by decreasing the salt concentration.

We have shown excellent discrimination of one matched hybrid over a mismatched hybrids. However, in short oligonucleotide hybridization, signals from mismatched hybrids will always exist, with the majority of the mismatch hybrids resulting from end mismatch. This sets the limit on insert sizes that can be effectively examined by a probe of a certain length.

The influence of sequence complexity on discrimination cannot be ignored. However, the complexity effects are more significant when defining sequence information by short oligonucleotide hybridization for specific, nonrandom sequences, and can be overcome by using an appropriate probe to target length ratio. The length ratio is chosen to make unlikely, on statistical grounds, the occurence of specific sequences which have a number of end-mismatches which would be able to eliminate or falsely invert discrimination. Our results suggest the use of oligonucleotides 6, 7 and 8 nucleotides in length on target nucleic acid inserts no longer than 0.6, 2.5 and 10 kb, respectively.

7. EXAMPLE: SEQUENCING A TARGET USING OCTAMERS AND NONAMERS

In this example, hybridization conditions that were used are described supra in § 6. Data resulting from the hybridization of octamer and monomer oligonucleotides shows that sequencing by hybridization provides an extremely high degree of accuracy. In this experiment, a known sequence was used to predict a series of contiguous overlapping component octamer and nonamer oligonucleotides.

In addition to the perfectly matching oligonucleotides, mismatch oligonucleotides wherein internal or end mismatches would occur in the duplex formed by the oligonucleotide and the target were examined. In these analyses, the lowest practical temperature was used to maximize hybridization formation. Washes were accomplished at the same or lower temperatures to ensure maximal discrimination by utilizing the greater dissociation rate of mismatch versus matched oligonucleotide/target hybridization. These conditions are shown to be applicable to all sequences although the absolute hybridization yield is shown to be sequence dependent.

The least distabilizing mismatch that can be postulated is a simple end mismatch, so that the test of sequencing by hybridization is the ability to discriminate perfectly matched oligonucleotide/target duplexes from end-mismatched oligonucleotide/target duplexes.

The discrimination values for 102 of 105 hybridizing oligonucleotides in a dot blot format were greater than 2 allowing a highly accurate generation of the sequence. This system also allowed an analysis of the effect of sequence on hybridization formation and hybridization instability.

One hundred base pairs of a known portion of a human β-interferon genes prepared by PCR i.e. the 100 bp target sequence, was generated with data resulting from the hybridization of 105 oligonucleotides probes of known sequence to the target nucleic acid. The oligonucleotide probes used included 72 octamer and 21 nonamer oligonucleotides whose sequence was perfectly complementary to the target. The set of 93 probes provided consecutive overlapping frames of the target sequence displaced by one or two bases as described in FIG. 8.

To evaluate the effect of mismatches, hybridization was examined for 12 additional probes that contained at least one end mismatch when hybridized to the 100 bp test target sequence. Also tested was the hybridization of twelve probes with target end-mismatch to four other control nucleic acid sequences chosen so that the 12 oligonucleotides could form perfectly matched duplex hybrids with the four control DNAs. Thus, the hybridization of internal mismatched, end-mismatched and perfectly matched duplex pairs of oligonucleotide and target were evaluated for each oligonucleotide used in the experiment.

The effect of absolute DNA target concentration on the hybridization with the test octamer and nonamer oligonucleotides was determined by defining target DNA concentration by detecting hybridization of a different oligonucleotide probe to a single occurence non-target site within the co-amplified plasmid DNA.

The results of this experiment showed that all oligonucleotides containing perfect matching complementary sequence to the target or control DNA hybridized more strongly than those oligonucleotides having mismatches. To come to this conclusion we examined Hp and D values for each probe. Hp defines the amount of hybrid duplex formed between a test target and an oligonucleotide probe. By assigning values of between 0 and 10 to the hybridization obtained for the 105 probes, it was apparent that 68.5% of the 105 probes had an HP greater than 2.

Discrimination (D) values were obtained where D was defined as the ratio of signal intensities between 1) the dot containing a perfect matched duplex formed between test oligonucleotide and target or control nucleic acid and 2) the dot containing a mismatch duplex formed between the same oligonucleotide and a different site within the target or control nucleic acid. Variations in the value of D result from either 1) perturbations in the hybridization efficiency which allows visualization of signal over background, or 2) the type of mismatch found between the test oligonucleotide and the target. The D values obtained in this experiment were between 2 and 40 for 102 of the 105 oligonucleotide probes examined. Calculations of D for the group of 102 oligonucleotides as a whole showed the average D was 10.6.

There were 20 cases where oligonucleotide/target duplexes exhibited an end-mismatch. In five of these, D was greater than 10. The large D value in these cases is most likely due to hybridization destabilization caused by other than the most stable (G/T and G/A) end mismatches. The other possibility is there was an error in the sequence of either the oligonucleotides or the target.

Error in the target for probes with low Hp was excluded as a possibility because such an error would have affected the hybridization of each of the other eight overlapping oligonucleotides. There was no apparent instability due to sequence mismatch for the other overlapping oligonucleotides, indicating the target sequence was correct.

Error in the oligonucleotide sequence was excluded as a possibility after the hybridization of seven newly synthesized oligonucleotides was re-examined. Only 1 of the seven oligonucleotides resulted in a better D value.

Low hybrid formation values of Hp could result from hybrid instability or from an inability to form hybrid duplex. An inability to form hybrid duplexes would result from either 1) self complementarity of the chosen probe or 2) target/target self hybridization. Oligonucleotide/oligonucleotide duplex formation could be favored over oligonucleotide/target hybrid duplex formation if the probe was self-complementary. Similarly, target/target association could be favored if the target was self-complementary or could form internal palindromes. In evaluating these possibilities, it was apparent from probe analysis that the questionable probes were unable to form hybrids with themselves. Moreover, in examining the contribution of target/target hybridization, it was determined that one of the questionable oligonucleotide probes hybridized inefficiently with two different DNAs containing the same target. The low probability that two different DNAs would have a self-complementary region for the same target sequence lead to the conclusion that target/target hybridization did not contribute to low hybridization formation. Thus, these results indicate that hybrid instability and not the inability to form hybrids was the cause of the low hybrid formation observed for specific oligonucleotides. The results also indicate that low hybrid formation is due to the specific sequences of certain oligonucleotides. Moreover, the results indicate that reliable results can be obtained to generate sequences if octamer and nonamer oligonucleotides are used.

These results show that using thee methods described long sequences of any specific target nucleic acid can be generated by maximal and unique overlap of constituent oligonucleotides. Such sequencing methods are dependent on the content of the individual component oligomers regardless of their frequency and their position.

The sequence which is generated by computer using the algorithm described below is of high fidelity. The algorithm can tolerate false positive signals from the hybridization dots as is indicated from the fact the sequence generated from the 105 hybridization values, which included four less reliable values, was correct. This fidelity in sequencing by hybridization is due to the "all or none" kinetics of short oligonucleotide hybridization and the difference in duplex stability that exists between perfectly matched duplexes and mismatched duplexes. The ratio of duplex stability of matched and end-mismatched duplexes increases with decreasing duplex length. Moreover binding energy decreases with decreasing duplex length resulting in a lower hybridization efficiency. However, the results provided show that octamer hybridization allows the balancing of the factors affecting duplex stability and discrimination to produce a highly accurate method of sequencing by hybridization. Results presented in other sections show that oligonucleotides that are 6, 7 or 8 nucleotides can be effectively used to generate reliable sequence on targets that are 0.5 kb (for hexamers) 2 kb (for septamers) and 6 kB long (for octamers). The sequence of long fragments can be overlapped to generate a complete genome sequence.

The computer algorithm to determine sequence by hybridization is described in Appendix A.

APPENDIX A

Algorithm

This appendix describes an algorithm for generation of a long sequence written in a four letter alphabet from constituent k-tuple words in a minimal number of separate, randomly defined fragments of a starting nucleic acid sequence where K is the length of an oligonucleotide probe. The algorithm is primarily intended for use in the sequencing by hybridization (SBH) process. The algorithm is based on subfragments (SF), informative fragments (IF) and the possibility of using pools of physical nucleic sequences for defining informative fragments.

As described in Appendix A, subfragments can be caused by branch points in the assembly process resulting from the repetition of a K−1 oligomer sequence in a target nucleic acid. Subfragments are sequence fragments found between any two repetitive words of the length K−1 that occur in a sequence. Multiple occurrences of K−1 words are the cause of interruption of ordering the overlap of K-words in the process of sequence generation. Interruption leads to a sequence remaining in the form of subfragments. Thus, the unambiguous segments between branching points whose order can not be uniquely determined are called sequence subfragments.

In Appendix A informative fragments are defined as fragments of a sequence that are determined by the nearest ends of overlapped physical sequence fragments.

A certain number of physical fragments can be pooled without losing the possibility of defining informative fragments. The total length of randomly pooled fragments depends on the length of k-tuples that are used in the sequencing process.

The algorithm consists of two main units. The first part is used for generation of subfragments from the set of k-tuples contained in a sequence. Subfragments can be generated within the coding region of physical nucleic acid sequence of certain sizes, or within the informative fragments defined within long nucleic acid sequences. Both types of fragments are members of the basic library. This algorithm does not describe the determination of the content of the k-tuples of the informative fragments of the basic library, i.e. the step of preparation of informative fragments to be used in the sequence generation process.

The second part of the algorithm determines the linear order of obtained subfragments with the purpose of regenerating the complete sequence of the nucleic acid fragments of the basic library. For this purpose a second, ordering library is used, made of randomly pooled fragments of the starting sequence. The algorithm does not include the step of combining sequences of basic fragments to regenerate an entire, megabase plus sequence. This can be accomplished using the link-up of fragments of the basic library which is a prerequisite for informative fragment generation. Alternatively it can be accomplished after generation of sequences of fragments of the basic library by this algorithm, using search for their overlap, based on the presence of common end-sequences.

The algorithm requires neither knowledge of the number of appearances of a given K-tuple in a nucleic acid sequence of the basic and ordering libraries, nor does it require the information of which k-tuple words are present on the ends of a fragment. The algorithm operates with the mixed content of k-tuples of various length. The concept of the algorithm enables operations with the k-tuple sets that contain false positive and false negative k-tuples. Only in specific cases does the content of the false k-tuples primarily influence the completeness and correctness of the generated sequence. The algorithm can be used for optimization of parameters in simulation experiments, as well as for sequence generation in the actual SBH experiments e.g. generation of the genomic DNA sequence. In optimization of parameters, the choice of the oligonucleotide probes (k-tuples) for practical and convenient fragments and/or the choice of the optimal lengths and the number of fragments for the defined probes are especially important.

SYSTEMS AND METHODS

The algorithm is implemented on an IBM PC/AT compatible computer running under MSDOS 3.30 System works on the clock frequency of 6 or 10 MHz. The workstation is equipped with one 360 kb–1.2 Mb floppy disk drive, and a 40 Mb hard disk, formatted as two 8 Mb and 32 Mb partitions.

The software is written using Microsoft's QuickBasic Compiler, version 2.0. It does not require any graphics facilities.

1. Generation of Subfragments

This part of the algorithm has a central role in the process of the generation of the sequence from the content of k-tuples. It is based on the unique ordering of k-tuples by means of maximal overlap. The main obstacles in sequence generation are specific repeated sequences and false positive and/or negative k-tuples. The aim of this part of the algorithm is to obtain the minimal number of the longest possible subfragments, with correct sequence. This part of the algorithm consists of one basic, and several control steps. A two-stage process is necessary since certain information can be used only after generation of all primary subfragments.

1.1. Generation of Primary Subfragments or pSFs

The main problem of sequence generation is obtaining a repeated sequence from word contents that by definition do not carry information on the number of occurrences of the particular k-tuples. The concept of the entire algorithm depends on the basis on which this problem is solved. In principle, there are two opposite approaches: 1. repeated sequences can be obtained at the beginning, in the process of generation of pSFs, or 2. repeated sequences can be obtained later, in the process of the final ordering of the subfragments. In the first case, pSFs contain an excess of sequences and in the second case, they contain a deficit of sequences. The first approach requires elimination of the excess sequences generated, and the second requires permitting multiple use of some of the subfragments in the process of the final assembling of the sequence.

The difference in the two approaches is in the degree of strictness of the rule of unique overlap of k-tuples. The less severe rule is: k-tuple X is unambiguously maximally overlapped with k-tuple Y if and only if, the rightmost K−1 end of k-tuple X is present only on the leftmost end of k-tuple Y. This rule allows the generation of repetitive sequences and the formation of surplus sequences.

A stricter rule which is used in the second approach has an additional caveat: k-tuple X is unambiguously maximally overlapped with k-tuple Y if and only if, the rightmost K−1 end of k-tuple X is present only on the leftmost end of k-tuple Y and if the leftmost K−1 end of k-tuple Y is not present on the rightmost end of any other k-tuple. The algorithm based on the stricter rule is simpler, and is described herein.

FIG. 10 show the minimal conditions for unique overlap, or conversely stopping the process of elongation of a given subfragment. The process is stopped when the right k−1 end of the last k-tuple included is not present on the left end of any k-tuple (FIG. 10.1) or is present on two or more k-tuples (FIG. 10.2). If it is present on only one k-tuple the second part of the rule is tested (FIG. 10.3 and 10.4). If in addition there is a k-tuple which differs from the previously included one, the assembly of the given subfragment is terminated only on the first leftmost position (FIG. 10.3). If this additional k-tuple does not exist, the conditions are met for unique k−1 overlap and a given subfragment is extended to the right by one element.

Beside the basic rule, a supplementary one is used to allow the usage of k-tuples of different lengths. The maximal overlap is the length of k−1 of the shorter k-tuple of the overlapping pair. Generation of the pSFs is performed starting from the first k-tuple from the file in which k-tuples are displayed randomly and independently from their order in a nucleic acid sequence. Thus, the first k-tuple in the file is not necessarily on the beginning of the sequence, nor on the start of the particular subfragment. The process of subfragment generation is performed by ordering the k-tuples by means of unique overlap, which is defined by the described rule. Each used k-tuple is erased from the file. At the point when there are no further k-tuples unambiguously overlapping with the last one included, the building of subfragment is terminated and the buildup of another pSF is started. Since generation of a majority of subfragments does not begin from their actual starts, the formed pSF are added to the k-tuple file and are considered as a longer k-tuple. Another possibility is to form subfragments going in both directions from the starting k-tuple. The process ends when further overlap, i.e. the extension of any of the subfragments, is not possible.

The pSFs can be divided in three groups: 1) Subfragments of the maximal length and correct sequence in cases of exact k-tuple set; 2) short subfragments, formed due to the use of the maximal and unambiguous overlap rule on the incomplete set, and/or the set with some false positive k-tuples; and 3) pSFs of an incorrect sequence. The incompleteness of the set in 2) is caused by false negative results of a hybridization experiment, as well as by using an incorrect set of k-tuples. These are formed due to the false positive and false negative k-tuples and can be: a) misconnected subfragments; b) subfragments with the wrong end; and c) false positive k-tuples which appears as false minimal subfragments.

Considering false positive k-tuples, there is the possibility for the presence of a k-tuple containing more than one wrong base or containing one wrong base somewhere in the middle, as well as the possibility for a k-tuple with a wrong base on the end. Generation of short, erroneous or misconnected subfragments is caused by the latter k-tuples. The k-tuples of the former two kinds represent wrong pSFs with length equal to k-tuple length.

Several more common examples of obtaining short subfragments with or without a wrong base at the end because of errors in the k-tuple set are shown in FIG. 11. In the case of one false negative k-tuple (as shown in FIG. 11A), pSFs are generated because of the impossibility of maximal overlapping (FIG. 10.1). In the case of the presence of one false positive k-tuple with the wrong base on its leftmost or rightmost end (either end in FIG. 11.B), pSFs are generated because of the impossibility of unambiguous overlapping (FIGS. 10, 11 and 12). When both false positive and false negative k-tuples with a common k–1 sequence are present in the file, pSFs are generated, and one of these pSFs contains the wrong k-tuple at the relevant end (FIG. 11C).

The process of correcting subfragments with errors in sequence and the linking of unambiguously connected pSF is performed after subfragment generation and in the process of subfragment ordering. The first step which consists of cutting the misconnected pSFs and obtaining the final subfragments by unambiguous connection of pSFs is described below.

1.2. Recognition and Treatment of Misconnected Subfragments

We have defined two possibilities for the formation of misconnected subfragments. All variations of these two possibilities are shown in FIG. 12. In the first (demonstrated as column I in FIG. 12) a mistake occurs when an erroneous k-tuple appears on the points of assembly of the repeated sequences of lengths k–1. In the second, the repeated sequences are shorter than k–1 (FIG. 12, column II). These situations can occur in two variants each. In the first variant, one of the repeated sequences represents either end of a fragment (FIG. 12-A and B for column I and FIG. 12-E for column II). In the second variant, the repeated sequence occurs at any position within the fragment (FIG. 12-C and D for column I and FIG. 12-F for column II). For the first possibility, the absence of some k-tuples from the file (false negatives) is required to generate a misconnection. The second possibility requires the presence of both false negative and false positive k-tuples in the file. Considering the repetitions of k–1 sequence, the lack of only one k-tuple is sufficient when either end is repeated internally as shown in FIG. 12-A and B. The lack of two is needed for strictly internal repetition (FIG. 12-C and D). The reason is that the end of a sequence can be considered informatically as an endless linear array of false negative k-tuples. From the "smaller than k–1 case", only the repeated sequence of the length of k–2, which requires two (FIG. 12-E) or three (FIG. 12-F) specific erroneous k-tuples, will be considered. It is very likely that these will be the only cases which will be detected in a real experiment, the others being much less frequent.

Recognition of the misconnected subfragments is more strictly defined when a repeated sequence does not appear at the end of the fragment. In this situation, one can detect further two subfragments, one of which contains on its leftmost (FIG. 12-D), and the other on its rightmost end (FIG. 12-C and D and FIG. 12-F) k–2 sequences which are also present in the misconnected subfragment. When the repeated sequence is on the end of the fragment, there is only one subfragment which contains k–2 sequence causing the mistake in subfragment formation on its leftmost or rightmost end (as shown in FIG. 12-A and B and FIG. 12-E).

The removal of misconnected subfragments by their cutting is performed according to the common rule: If the leftmost or rightmost sequence of the length of k–2 of any subfragments is present in any other subfragment, the subfragment is to be cut into two subfragments, each of them containing k–2 sequence. This rule does not cover rarer situations of a repeated end when there are more than one false negative k-tuple on the point of repeated k–1 sequence. Misconnected subfragments of this kind can be recognized by using the information from the overlapped fragments, or informative fragments of both the basic and ordering libraries. In addition, the misconnected subfragment will remain when two or more false negative k-tuples occur on both positions which contain the identical k–1 sequence. This is a very rare situation since it requires at least 4 specific false k-tuples. An additional rule can be introduced to cut these subfragments on sequences of length k if the given sequence can be obtained by combination of sequences shorter than k–2 from the end of one subfragment and the start of another.

By strict application of the described rule, some completeness is lost to ensure the accuracy of the output. Some of the subfragments will be cut although they are not misconnected, since they fit into the pattern of a misconnected subfragment. There are several situations of this kind. For example, a fragment, beside at least two identical k–1 sequences, contains any k–2 sequence from k–1 or a fragment contains k–2 sequence repeated at least twice and at least one false negative k-tuple containing given k–2 sequence in the middle, etc.

1.3. Merging of the pSFs into Longer Subfragments

The aim of this part of the algorithm is to reduce the number of pSFs to a minimal number of longer subfragments with correct sequence. The generation of unique longer subfragments or a complete sequence is possible in two situations. The first situation concerns the specific order of repeated k–1 words. There are cases in which some or all maximally extended pSFs (the first group of pSFs) can be uniquely ordered. For example in fragment S-R1-a-R2-b-R1-c-R2-E where S and E are the start and end of a fragment, a, b and c are different sequences specific to respective subfragments and R1 and R2 are two k–1 sequences that are tandemly repeated, five subfragments are generated (S-R1, R1-a-R2, R2-b-R1, R1-c-R2 and R2-E). They can be ordered in two ways; the original sequence above or S-R1-c-R2-b-R1-a-R2-E. In contrast, in a fragment with the same number and types of repeated sequences but ordered differently, i.e. S-R1-a-R1-b-R2-c-R2-E, there is no other sequence which includes all subfragments. Examples of this type can be recognized only after the process of generation of pSFs. They represent the necessity for two steps in the process of pSF generation. The second situation of generation of false short subfragments on positions of nonrepeated k–1 sequences when the files contain false negative and/or positive k-tuples is more important (second and third group of pSF, see FIG. 4.

The solution for both pSF groups consists of two parts. First, the false positive k-tuples appearing as the nonexisting minimal subfragments are eliminated. All k-tuple subfragments of length k which do not have an overlap on either end, of the length of longer than k–a on one end and longer than k–b on the other end, are eliminated to enable formation of the maximal number of connections. In our experiments, the values for a and b of 2 and 3, respectively, appeared to be adequate to eliminate a sufficient number of false positive k-tuples.

The merging of subfragments that can be uniquely connected is accomplished in the second step. The rule for connection is: two subfragments can be unambiguously connected if, and only if, the overlapping sequence at the relevant end or start of two subfragments is not present at the start and/or end of any other subfragment.

The exception is if one subfragment from the considered pair has the identical beginning and end. In that case connection is permitted, even if there is another subfragment with the same end present in the file. The main problem here is the precise definition of overlapping sequence. The connection is not permitted if the overlapping sequence unique for only one pair of subfragments is shorter than k–2, of if it is k–2 or longer but an additional subfragment exists with the overlapping sequence of any length longer than k−4. Also, both the conanical ends of pSFs and the ends after omitting one (or few) last bases are considered as the overlapping sequences.

After this step some false positive k-tuples (as minimal subfragments) and some subfragments with a wrong end can survive. In addition, in very rare occasions where a certain number of some specific false k-tuples are simultaneously present, an erroneous connection can take place. These cases will be detected and solved in the subfragment ordering process, and in the additional control steps along with the handling of uncut "misconnected" subfragments.

The short subfragments that are obtained are of two kinds. In the common case, these subfragmentss can be unambiguously connected among themselves because of the distribution of repeated k−1 sequences. This can be done only after the process of generation of pSFs and is a good example of the necessity for two steps in the process of pSF generation. In the case of using the file containing false positive and/or false negative k-tuples, short pSFs are obtained on the sites of nonrepeated k−1 sequences. Considering false positive k-tuples, there is possibility of presence of the k-tuple containing more than one wrong base (or containing one wrong base somewhere in the middle), as well as k-tuple with wrong base on the end. Generation of short and erroneous (or misconnected) subfragments is caused by the latter k-tuples. The k-tuples of the former kind represent wrong pSFs with length equal to k-tuple length.

The aim of merging pSF part of the algorithm is the reduction of the number of pSFs to the minimal number of longer subfragments with the correct sequence. All k-tuple subfragments that do not have an overlap on either end, of the length of longer than k−a on one, and longer than k−b on the other end, are eliminated to enable the maximal number of connections. In this way, the majority of false positive k-tuples are discarded. The rule for connection is: two subfragments can be unambiguously connected if, and only if the overlapping sequence of the relevant end or start of two subfragments is not present on the start and/or end of any other subfragment. The exception is a subfragment with the identical beginning and end. In that case connection is permitted, provided that there is another subfragment with the same end present in the file. The main problem here is of precise definition of overlapping sequence. The presence of at least two specific false negative k-tuples on the points of repetition of k−1 or k−2 sequences, as well as combining of the false positive and false negative k-tuples can destroy or "mask" some overlapping sequences and can produce an unambiguous, but wrong connection of pSFs. To prevent this, completeness must be sacrificed on account of exactness: the connection is not permitted on the end-sequences shorter than k−2, and in the presence of an extra overlapping sequence longer than k−4. The overlapping sequences are defined from the end of the pSFs, or omitting one, or few last bases.

In the very rare situations, with the presence of a certain number of some specific false positive and false negative k-tuples, some subfragments with the wrong end can survive, some false positive k-tuples (as minimal subfragments) can remain, or the erroneous connection can take place. These cases are detected and solved in the subfragments ordering process, and in the additional control steps along with the handling of uncut, misconnected subfragments.

2. Generation of the Sequence by the Ordering of Subfragments

The process of ordering of subfragments is similar to the process of their generation. If one considers subfragments as longer k-tuples, ordering is performed by their unambiguous connection via overlapping ends. The informational basis for unambiguous connection is the division of subfragments generated in fragments of the basic library into groups representing segments of those fragments. The method is analogous to the biochemical solution of this problem based on hybridization with longer oligonucleotides with relevant connecting sequence. The connecting sequences are generated as subfragments using the k-tuple sets of the appropriate segments of basic library fragments. Relevant segments are defined by the fragments of the ordering library that overlap with the respective fragments of the basic library. The shortest segments are informative fragments of the ordering library. The longer ones are several neighboring informative fragments or total overlapping portions of fragments corresponding of the ordering and basic libraries. In order to decrease the number of separate samples, fragments of the ordering library are randomly pooled, and the unique k-tuple content is determined.

Although we do not use longer k-tuples, it is possible to generate the connecting sequences for two reasons. First, by using the large number of fragments in the ordering library very short segments are generated, thus reducing the chance of the multiple appearance of the k−1 sequences which are the reasons for generation of the subfragments. Second, longer segments, consisting of the various regions of the given fragment of the basic library, do not contain some of the repeated k−1 sequences. In every segment a connecting sequence (a connecting subfragment) is generated for a certain pair of the subfragments from the given fragment. The process of ordering consists of three steps: (1) generation of the k-tuple contents of each segment; (2) generation of subfragments in each segment; and (3) connection of the subfragments of the fragment of the basic library using subfragments of the segments. Primary segments are defined as significant intersections and differences of k-tuple contents of a given fragment of the basic library with the k-tuple contents of the pools of the ordering library. Secondary (shorter) segments are defined as intersections and differences of the k-tuple contents of the primary segments.

There is a problem of accumulating both false positive and negative k-tuples in both the differences and Intersections. The false negative k-tuples from starting sequences accumulate in the intersections (overlapping parts), as well as false positive k-tuples occurring randomly in both sequences, but not in the relevant overlapping region. On the other hand, the majority of false positives from either of the starting sequences is not taken up into intersections. This is an example of the reduction of experimental errors from individual fragments by using information from fragments overlapping with them. The false k-tuples accumulate in the differences for another reason. The set of false negatives from the original sequences are enlarged for false positives from intersections and the set of false positives for those k-tuples which are not included in the intersection by error, i.e. are false negatives in the intersection. If the starting sequences contains 10% false negative data, the primary and secondary intersections will contain 19% and 28% false negative k-tuples, respectively. On the other hand, a mathematical expectation of 77 false positives can be predicted if the basic fragment and the pools have lengths of 500 bp and 10,000 bp, respectively. However, there is a possibility of recovering most of the "lost" k-tuples and of eliminating most of the false positive k-tuples.

First, one has to determine a basic content or the k-tuples for a given segment as the intersection of a given pair of the k-tuple contents. This is followed by including all k-tuples of the starting k-tuple contents in the intersection, which contain at one end k−1 and at the other end k−+ sequences which occur at the ends of two k-tuples of the basic set. This is done before generation of the differences thus preventing the accumulation of false positives in that process. Following that, the same type of enlargement of k-tuple set is applied to differences with the distinction that the borrowing is from the intersections. All borrowed k-tuples are eliminated from the intersection files as false positives.

The intersection—a set of common k-tuples— is defined for each pair (a basic fragment)×(a pool of ordering library). If the number of k-tuples in the set is significant it is enlarged with the false negatives according to the described rule. The primary difference set is obtained by subtracting from a given basic fragment the obtained intersection set. The false negative k-tuples are appended to the difference set by borrowing from the intersection set according to the described rule and, at the same time, removed from the intersection set as false positive k-tuples. When the basic fragment is longer than the pooled fragments this difference can represent the two separate segments which somewhat reduces its utility in further steps. The primary segments are all generated intersections and differences of pairs (a basic fragment)×(a pool of ordering library) containing the significant number of k-tuples. k-tuple sets of secondary segments are obtained by comparison of k-tuple sets of all possible pairs of primary segments. The two differences are defined for each pair which produces the intersection with the significant number of k-tuples. The majority of available information from overlapped fragments is recovered in this step so that there is little to be gained from the third round of forming intersections and differences.

(2) Generation of the subfragments of the segments is performed identically as described for the fragments of the basic library.

(3) The method of connection of subfragments consists of sequentially determining the correctly linked pairs of subfragments among the subfragments from a given basic library fragment which have some overlapped ends. In the case of 4 relevant subfragments, two of which contain the same beginning and two having the same end, there are 4 different pairs of subfragments that can be connected. In general 2 are correct and 2 are wrong. To find correct ones, the presence of the connecting sequence of each pair is tested in the subfragments generated from all primary and secondary segments for a given basic fragment. The length and the position of the connecting sequence are chosen to avoid interference with sequences which occur by chance. They are k+2 or longer, and include at least one element 2 beside overlapping sequence in both subfragments of a given pair. The connection is permitted only if the two connecting sequences are found and the remaining two do not exist. The two linked subfragments replace former subfragments in the file and the process is cyclically repeated.

As mentioned in the section "Generation of pSFs", repeated sequences have to be generated in this step. This means that some subfragments have to be included in linked subfragments more than once. They will be recognized by finding the relevant connecting sequence which engages one subfragment in connection with two different subfragments.

The recognition of misconnected subfragments generated in the processes of building pSFs and merging pSFs into longer subfragments is based on testing whether the sequences of subfragments from a given basic fragment exist in the sequences of subfragments generated in the segments for the fragment. The sequences from an incorrectly connected position will not be found indicating the misconnected subfragments.

Beside the described three steps in ordering of subfragments some additional control steps or steps applicable to specific sequences will be necessary for the generation of more complete sequence without mistakes.

The determination of which subfragment belongs to which segment is performed by comparison of contents of k-tuples in segments and subfragments. Because of the errors in the k-tuple contents (due to the primary error in pools and statistical errors due to the frequency of occurrences of k-tuples) the exact partitioning of subfragments is impossible. Thus, instead of "all or none" partition, the chance of coming from the given segment (P(sf,s)) is determined for each subfragment. This probability is the function of the lengths of k-tuples, the lengths of subfragments, the lengths of fragments of ordering library, the size of the pool, and of the percentage of false k-tuples in the file:

$$P(sf,s) = (Ck - F)/Lsf,$$

where Lsf is the length of subfragment, Ck is the number of common k-tuples for a given subfragment/segment pair, and F is the parameter that includes relations between lengths of k-tuples, fragments of basic library, the size of the pool, and the error percentage.

Subfragments attributed to a particular segment are treated as redundant short pSFs and are submitted to a process of unambiguous connection. The definition of unambiguous connection is slightly different in this case, since it is based on a probability that subfragments with overlapping end(s) belong to the segment considered. Besides, the accuracy of unambiguous connection is controlled by following the connection of these subfragments in other segments. After the connection in different segments, all of the obtained subfragments are merged together, shorter subfragments included within longer ones are eliminated, and the remaining ones are submitted to the ordinary connecting process. If the sequence is not regenerated completely, the process of partition and connection of subfragments is repeated with the same or less severe criterions of probability of belonging to the particular segment, followed by unambiguous connection.

Using severe criteria for defining unambiguous overlap, some information is not used. Instead of a complete sequence, several subfragments that define a number of possibilities for a given fragment are obtained. Using less severe criteria an accurate and complete sequence is generated. In a certain number of situations, e.g. an erroneous connection, it is possible to generate a complete, but an incorrect sequence, or to generate "monster" subfragments with no possible connection among them. Thus, for each fragment of the basic library one obtains: a) several possible solutions where one is correct and b) the most probable correct solution. Also, in a very small number of cases, due to the mistake in the subfragment generation process or due to the specific ratio of the probabilities of belonging, it is impossible to generate any unambiguous solution or one, the most probable solution. These cases will remain as incomplete sequences, or the unambiguous solution will be obtained by comparing these data with other, overlapped fragments of basic library.

3. Implementation

The described algorithm is tested on a randomly generated, 50 kb sequence, containing 40% GC to simulate the GC content of the human genome. In the middle part of this sequence were inserted various Alu, and some other repetitive sequences, of a total, length of about 4 kb. To simulate an in vitro SBH experiment, the following operations were performed to prepare appropriate data.

Positions of 60 5 kb overlapping "clones" were randomly defined, to simulate preparation of basic library:

Positions of 1000 500 bp "clones" were randomly determined, to simulate making the ordering library. These fragments were extracted from the sequence. Random pools of 20 fragments were made, and k-tuple sets of pools were determined and stored on the hard disk. These data are used in the subfragment ordering phase: For the same density of clones 4 million clones in basic library and 3 million clones in ordering library will be needed for the entire human genome. The total number of 7 million clones is several fold smaller than the number of clones a few kb long that are needed for random cloning of almost all of genomic DNA and its sequencing by a gel-based method.

From the data on the starts and ends of 5 kb fragments, we determined 117 "informative fragments" in the sequence. This was followed by determination of sets of overlapping k-tuples of which the single "informative fragment" consist. Only the subset of k-tuples matching our predetermined list were used. The list contains 65% 8-mers, 30% 9-mers and 5% 10–12-mers. We performed processes of generation and the ordering of subfragments on these data.

The testing of the algorithm was performed on the simulated data in two experiments. The sequence of 50 informative fragments was regenerated with the 100% correct data set (over 20,000 bp), and 26 informative fragments (about 10,000 bp) with 10% false k-tuples (5% positive and 5% negative ones).

In the first experiment all subfragments were correct and in only one out of 50 informative fragments the sequence was not completely regenerated but remained in the form of 5 subfragments. The analysis of positions of overlapped fragments of ordering library has shown that they lack the information for the unique ordering of the 5 subfragments. The subfragments can be connected in two possible ways based on overlapping ends, 1-2-3-4-5 and 1-4-3-2-5. The only difference is the exchange of positions of subfragments 2 and 4. Since subfragments 2,3, and 4 are relatively short (total of about 100 bp), the relatively greater chance existed, and occurred in this case, that none of the fragments of ordering library started or ended in the subfragment 3 region.

To simulate real sequencing, we included some false ("hybridization") data as input in a number of experiments. In oligomer hybridization experiments, under proposed conditions the only situation possibly producing unreliable data is the end mismatch versus full match hybridization. Therefore, in simulation we considered as false positives only those k-tuples differing in a single element on either end from the real one. These "false" sets are made as follows. On the original set of a k-tuples of the informative fragment, a subset of 5% false positive k-tuples are added. False positive k-tuples are made by randomly picking a k-tuple from the set, copying it and altering a nucleotide on its beginning or end. This is followed by subtraction of a subset of 5% randomly chosen k-tuples. In this way the statistically expected number of the most complicated cases is generated in which the correct k-tuple is replaced with a k-tuple with the wrong base on the end.

Production of k-tuple sets as described leads to up to 10% of false data. This value varies from case to case, due to the randomness of choice of k-tuples to be copied-altered, and erased. Nevertheless, this percentage 3–4 times exceeds the amount of unreliable data in real hybridization experiments. The introduced error of 10% leads to the two fold increase in the number of subfragments both in fragments of basic library (basic library informative fragments) and in segments. About 10% of the final subfragments have a wrong base at the end as expected for the k-tuple set which contains false positives (see generation of primary subfragments). Neither the cases of misconnection of subfragments nor subfragments with wrong sequence were observed. In 4 informative fragments out of 26 examined in the ordering process the complete sequence was not regenerated. In all 4 cases the sequence was obtained in the form of several longer subfragments and several shorter subfragments contained in the same segment. This result shows that the algorithmic principles allow working with a large percentage of false data.

4. Discussion

The success of the generation of the sequence from its k-tuple content can be described in terms of completeness and accuracy. In the process of generation, two particular situations can be defined: 1) Some part of the information is missing in the generated sequence, but one knows where the ambiguities are and to which type they belong, and 2) the regenerated sequence that is obtained does not match the sequence from which the k-tuple content is generated, but the mistake can not be detected. Assuming the algorithm is developed to its theoretical limits, as in the use of the exact k-tuple sets, only the first situation can take place. There the incompleteness results in a certain number of subfragments that can not be ordered unambiguously and the impossibility of determination of the exact length of monotonous sequences, i.e. number of perfect tandem repeats.

With false k-tuples, there is also the possibility of generating incorrect sequence. The reason for mistakes does not lie in the shortcomings of the algorithm, but in the fact that a given content of k-tuples unambiguously represents the sequence that differs from the original one. One can define three classes of error, depending on the kind of the false k-tuples present in the file. False negative k-tuples (which are not accompanied with the false positives) are producing "deletions". False positive k-tuples are producing "elongations (unequal crossing over)". False positives accompanied with false negatives are the reason for generation of "insertions", alone or combined with "deletions". The deletions are produced when all of the k-tuples (or their majority) between two possible starts of the subfragments are false negatives. Since every position in the sequence is defined by k k-tuples, the occurrence of the deletions in a common case requires k consecutive false negatives. (With 10% of the false negatives and k=8, this situation takes place after every $10^8$ elements). This situation will be extremely infrequent even in mammalian genome sequencing using random libraries containing ten genome equivalents.

Elongation of the end of the sequence caused by false positive k-tuples is the special case of "insertions", since the end of the sequence can be considered as the endless linear array of false negative k-tuples. One can consider a group of false positive k-tuples producing subfragments longer than one k-tuple. Situations of this kind can be detected if subfragments are generated in overlapped fragments, like random physical fragments of the ordering library. An insertion, or insertion in place of a deletion, can arise as a result of specific combinations of false positive and false negative k-tuples. In the first case the number of consecutive false negatives has to be smaller than k. Both cases require several overlapping false positive k-tuples. The insertions and deletions are mostly theoretical possibilities without sizable practical repercussions since the requirements in the number and specificity of false k-tuples are simply too high.

In every other situation of not meeting the theoretical requirement of the minimal number and the kind of the false positives and/or negatives, mistakes in the k-tuples content can produce only the lesser completeness of a generated sequence.

We claim:

1. A plurality of oligonucleotides capable of hybridizing to complementary DNA or RNA, each oligonucleotide in the plurality comprising an informative region of predetermined sequence and consisting of at least 6 nucleotides, said plurality comprising a majority of or all possible informative regions of a given length.

2. The plurality of oligonucleotides of claim 1, wherein said oligonucleotides have non-informative bases on one or both ends.

3. The plurality of oligonucleotides of claims 1 or 2, wherein said oligonucleotides have at least one nucleotide analog or at least one base analog.

4. A plurality of oligonucleotides capable of hybridizing to complementary DNA or RNA, each oligonucleotide in the plurality comprising an informative region of predetermined sequence and consisting of at least 6 nucleotides, said plurality comprising more than 4000 oligonucleotides.

5. The plurality of oligonucleotides of claim 4, wherein the oligonucleotides have non-informative bases on one or both ends.

6. The plurality of oligonucleotides of claims 4 or 5, wherein the oligonucleotides have at least one nucleotide analog or at least one base analog.

7. A plurality of oligonucleotides capable of hybridizing to complementary DNA or RNA, each having a predetermined sequence and a predetermined length, each oligonucleotide having a continuous sequence of at least five bases at its terminus overlapping with at least one other oligonucleotide at its opposite terminus in the plurality of oligonucleotides.

8. The plurality of oligonucleotides of claim 7, wherein the oligonucleotides are at least 6 nucleotides in length.

9. The plurality of oligonucleotides of claim 7, wherein said continuous overlapping sequence is at least 5 nucleotides in length.

10. The plurality of oligonucleotides of claims 7, 8 or 9, wherein the oligonucleotides have at least one nucleotide analog or at least one base analog.

* * * * *

SEQUENCE LISTING

<160> NUMBER OF SEQ ID NOS: 10

<210> SEQ ID NO 1
<211> LENGTH: 60
<212> TYPE: DNA
<213> ORGANISM: Artificial
<220> FEATURE:
<223> OTHER INFORMATION: subfragments in sequence hybridization by a
      hypothetical clone
<220> FEATURE:
<221> NAME/KEY: misc_feature
<222> LOCATION: (1)..(60)
<223> OTHER INFORMATION: n = g, a, t, or c

<400> SEQUENCE: 1
nnnnnnnctg gagtccctcg gttggctgta gcgagtccct gatttggctg actnnnnnnn    60

<210> SEQ ID NO 2
<211> LENGTH: 17
<212> TYPE: DNA
<213> ORGANISM: Artificial
<220> FEATURE:
<223> OTHER INFORMATION: subfragments in sequence hybridization by a
      hypothetical clone
<220> FEATURE:
<221> NAME/KEY: misc_feature
<222> LOCATION: (1)..(17)
<223> OTHER INFORMATION: n = g, a, t, or c

<400> SEQUENCE: 2
ttggctgact nnnnnnn                                                    17

<210> SEQ ID NO 3
<211> LENGTH: 17
<212> TYPE: DNA
<213> ORGANISM: Artificial
<220> FEATURE:
<223> OTHER INFORMATION: subfragments in sequence hybridization by a
      hypothetical clone

<400> SEQUENCE: 3
agtccctcgg ttggctg                                                    17

<210> SEQ ID NO 4
<211> LENGTH: 18
<212> TYPE: DNA
<213> ORGANISM: Artificial
<220> FEATURE:
<223> OTHER INFORMATION: subfragments in sequence hybridization by a
      hypothetical clone
<220> FEATURE:
<221> NAME/KEY: misc_feature
<222> LOCATION: (1)..(18)
<223> OTHER INFORMATION: n = g, a, t, or c

<400> SEQUENCE: 4
nnnnnnnctg gagtccct                                                   18

<210> SEQ ID NO 5
<211> LENGTH: 17
<212> TYPE: DNA
<213> ORGANISM: Artificial
<220> FEATURE:
<223> OTHER INFORMATION: subfragments in sequence hybridization by a
      hypothetical clone

<400> SEQUENCE: 5

```
agtccctgat ttggctg                                              17

<210> SEQ ID NO 6
<211> LENGTH: 19
<212> TYPE: DNA
<213> ORGANISM: Artificial
<220> FEATURE:
<223> OTHER INFORMATION: subfragments in sequence hybridization by a
      hypothetical clone

<400> SEQUENCE: 6
ttggctgtag cgagtccct                                            19

<210> SEQ ID NO 7
<211> LENGTH: 60
<212> TYPE: DNA
<213> ORGANISM: Artificial
<220> FEATURE:
<223> OTHER INFORMATION: subfragments in sequence hybridization by a
      hypothetical clone
<220> FEATURE:
<221> NAME/KEY: misc_feature
<222> LOCATION: (1)..(60)
<223> OTHER INFORMATION: n = g, a, t, or c

<400> SEQUENCE: 7
nnnnnnnctg gagtccctcg gttggctgta gcgagtccct gatttggctg actnnnnnnn    60

<210> SEQ ID NO 8
<211> LENGTH: 60
<212> TYPE: DNA
<213> ORGANISM: Artificial
<220> FEATURE:
<223> OTHER INFORMATION: subfragments in sequence hybridization by a
      hypothetical clone
<220> FEATURE:
<221> NAME/KEY: misc_feature
<222> LOCATION: (1)..(60)
<223> OTHER INFORMATION: n = g, a, t, or, c

<400> SEQUENCE: 8
nnnnnnnctg gagtccctga tttggctgta gcgagtccct cggttggctg actnnnnnnn    60

<210> SEQ ID NO 9
<211> LENGTH: 15
<212> TYPE: DNA
<213> ORGANISM: Artificial
<220> FEATURE:
<223> OTHER INFORMATION: subfragments in sequence hybridization by a
      hypothetical clone

<400> SEQUENCE: 9
accgtaaatg gatat                                                15

<210> SEQ ID NO 10
<211> LENGTH: 100
<212> TYPE: DNA
<213> ORGANISM: Homo sapiens

<400> SEQUENCE: 10
tttcagacaa gattcatcta gcactggctg gaatgagact attgttgaga acctcctggc    60
taatgtctat catcagataa accatctgaa gacagtcctg                         100
```